(12) United States Patent
Bondensgaard et al.

(10) Patent No.: US 8,211,420 B2
(45) Date of Patent: Jul. 3, 2012

(54) INTERLEUKIN-21 VARIANTS WITH ALTERED BINDING TO THE IL-21 RECEPTOR

(75) Inventors: Kent Bondensgaard, Vaerlose (DK); Lishan Kang, Beijing (CN); Siv Annegrethe Hjorth, Virum (DK); Dennis Madsen, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/520,057

(22) PCT Filed: Dec. 20, 2007

(86) PCT No.: PCT/EP2007/064326
§ 371 (c)(1),
(2), (4) Date: Feb. 2, 2010

(87) PCT Pub. No.: WO2008/074863
PCT Pub. Date: Jun. 26, 2008

(65) Prior Publication Data
US 2010/0196309 A1 Aug. 5, 2010

(30) Foreign Application Priority Data
Dec. 21, 2006 (EP) .................................. 06126901

(51) Int. Cl.
*C07K 14/435* (2006.01)
*A61K 45/00* (2006.01)
(52) U.S. Cl. ........................................ 424/85.2; 530/350
(58) Field of Classification Search .................. None
See application file for complete search history.

(56) References Cited

U.S. PATENT DOCUMENTS

| | | | |
|---|---|---|---|
| 4,902,502 A | 2/1990 | Nitecki et al. | |
| 5,494,662 A | 2/1996 | Kohji et al. | |
| 5,643,756 A | 7/1997 | Kayman et al. | |
| 6,307,024 B1 | 10/2001 | Novak et al. | |
| 6,423,685 B1 | 7/2002 | Drummond et al. | |
| 6,455,043 B1 | 9/2002 | Grillo-Lopez | |
| 6,929,932 B2 * | 8/2005 | Presnell et al. | 435/69.52 |
| 7,148,220 B2 | 12/2006 | Vite et al. | |
| 7,186,805 B2 * | 3/2007 | Presnell et al. | 530/351 |
| 7,250,274 B2 | 7/2007 | Chan et al. | |
| 7,276,478 B2 | 10/2007 | Sivakumar et al. | |
| 7,446,098 B2 * | 11/2008 | Fan | 514/44 R |
| 7,528,104 B2 | 5/2009 | Holmes et al. | |
| 2003/0003545 A1 | 1/2003 | Ebner et al. | |
| 2003/0108549 A1 | 6/2003 | Carter et al. | |
| 2003/0134390 A1 | 7/2003 | Presnell | |
| 2003/0186387 A1 | 10/2003 | Ebner et al. | |
| 2004/0009150 A1 | 1/2004 | Nelson et al. | |
| 2004/0228833 A1 | 11/2004 | Costantino et al. | |
| 2006/0024268 A1 | 2/2006 | Kasaian et al. | |

FOREIGN PATENT DOCUMENTS

| | | | |
|---|---|---|---|
| WO | WO 00/53761 | | 9/2000 |
| WO | WO 03/028630 | | 4/2003 |
| WO | WO/03/028630 | * | 4/2003 |
| WO | WO 03/040313 | | 5/2003 |
| WO | WO 03/082212 A2 | | 10/2003 |
| WO | WO/03/087320 | * | 10/2003 |
| WO | WO 03/087320 | | 10/2003 |
| WO | WO 03/103589 | | 12/2003 |
| WO | WO 2004/055168 | | 7/2004 |
| WO | WO 2004/112703 | | 12/2004 |
| WO | WO 2005/035565 | | 4/2005 |
| WO | WO 2005/052139 | | 6/2005 |
| WO | WO/2005/052139 | * | 6/2005 |
| WO | WO 2006/111524 | | 10/2006 |
| WO | WO 2006/135385 | | 12/2006 |
| WO | WO 2008/074863 | | 6/2008 |

OTHER PUBLICATIONS

Wells JA, Additivity of Mutational Effects in Proteins, Biochemistry, 29, 8509-8517, 1990.*
Ngo et al. Computational complexity, protein structure prediction, and the Levinthal paradox. The Protein Folding Problem and Tertiary Structure Prediction, pp. 492-495, 1994.*
Skolnick et al. From genes to protein structure and function: novel applications of computational approaches in the genomic era. Trends in Biotech 18(1): 34-39, 2000.*
Doerks et al. Protein annotation: detective work for function prediction. Trends in Genetics 14(6): 248-250, 1998.*
International Preliminary Report on Patentability issued Jun. 24, 2009 in corresponding International Application No. PCT/EP2007/064326.
Asao et al., "Cutting Edge: The Common y-Chain is an Indispensable Subunit of the IL-21 Receptor Complex[1]", The Journal of Immunology, Jul. 1, 2001, 167(1), 1-5.
Blohm et al., "Lack of Effector Cell Function and Altered Tetramer Binding of Tumor-Infiltrating Lymphocytes", The Journal of Immunology, Nov. 15, 2002, 169(10), 5522-5530.
Bondensgaard et al., "The Existence of Multiple Conformers of Interleukin-21 Directs Engineering of a Superpotent Analogue", The Journal of Biological Chemistry, Aug. 10, 2007, 282(32), 23326-23336.
Brandhuber et al., "Three-Dimensional Structure of Interleukin-2", Science 238, Dec. 18, 1987, 238(4834) 1707-1709.
Brandt et al., "The B7 Family Member B7-H6 is a tumor cell ligand for the activating natural killer cell receptor NKp30 in Humans," Journal Exp. Med., Jun. 15, 2009, 206(7), 1495-1503.
Brandt, C et al., Journal of Leukocyte Biology Suppl. S 119, Nov. 8-11, 2001, 2 pages.
Collins, et al., "IL-21 and IL-21 Receptor A New Cytokine pathway modulates innate and adaptive immunity", Immunological Research, 2003, 28(2), 131-140.
Communication from the EP Examining Division dated Jun. 3, 2009, Issued in corresponding EP Application No. 04762905.0, 8 pages.
Delgado et al., "Critical Reviews in Therapeutic Drug Carrier Systems", 1992, 9(3-4), 249-304.
Dunn et al., "Cancer Immunoediting: From Immunosurveillance to Tumor Escape", Nature Immunology, Nov. 2002, 3(11), 991-998.

(Continued)

*Primary Examiner* — Elly-Gerald Stoica
(74) *Attorney, Agent, or Firm* — Woodcock Washburn LLP

(57) ABSTRACT

The invention is concerned with IL-21 polypeptide variants having an altered binding to the common gamma chain (c) of the IL-21 receptor and the use thereof in therapy.

6 Claims, 4 Drawing Sheets

OTHER PUBLICATIONS

Genmab "Genmab Presents new Humax-CD20 and Humax-EFGr Pre-Clinical Data", Genmab New Release, Feb. 7, 2003, 1-3.

Hage et al., "Crystal Structure of the Interleukin-4/Receptor a Chain Complex Reveals a Mosaic Binding Interface", Cell Press, Apr. 16, 1999, 97(2), 271-281.

Kataki et al., "Tumor infiltrating lymphocytes and macrophages have a potential dual role in lung cancer by supporting both host-defense and tumor progression", Nov. 2002, 140(5), 320-328.

Katre, "The Conjugation of proteins with polyethylene glycol and other polymers: Altering properties of proteins to enhance their therapeutic potential", Advanced Drug Delivery Reviews, Jan.-Apr. 1993, 10(1), 91-114.

Khong et al., "Natural Selection of Tumor variants in the generation of "tumor escape" phenotypes", Nat. Immunol., Nov. 2002, 3(11), 999-1005.

Kinstler et al., "Mono-N-Terminal poly(ethylene glycol)-protein conjugates", Advanced Drug Delivery Reviews, Jun. 7, 2002, 54(4), 477-485.

Knauf et al., "Relationships of effective molecular size to systemic clearance in rats of recombinant interleukin-2 chemically modified with water-soluble polymers", J. Biol. Chem. Oct. 15, 1988, 263(29), 15064-15070.

Leonard et al., "Interleukin-21: A Modulator of Lymphoid Proliferation, Apoptosis and Differentiation", Nature Reviews Immunology, Sep. 2005, 5(9), 688-698.

Mehta et al., "Biology of IL-21 and the IL-21 Receptor", Immunological Reviews, Munksgaard XX, Dec. 2004, 202(1), 84-95.

Mott et al., "The Solution Structure of the F42A Mutant of Human Interleukin 2", Journal of Molecular Biology, Apr. 14, 1995 247(5), 979-994.

Olosz et al., "Structural Basis for Binding Multiple Ligands by the Common Cytokine Receptor Y-Chain", The Journal of Biological Chemistry, Jan. 28, 2002, 277(14), 12047-12052.

Parish-Novak et al., "Interleukin 21 and its receptor are involved in NK Cell expansion and Regulation of lymphocyte function", Nov. 2, 2000, 408(6808), 57-63.

Powers et al., "Three-Dimensional Solution Structure of Human Interleukin-4 by Multidimensional Heteronuclear Magnetic Resonance Spectroscopy", Science, Jun. 19, 1992, 256(5064), 1673-1677.

Response to the Jun. 3, 2009 Communication from the EP Examining Division EP04762905.0 dated Jan. 6, 2010, 6 pages.

Sivakumar et al., "Interleukin-21 is a T-Helper cytokine that regulates humoral immunity and cell mediated anti-tumor response", Immunology Black Well Publishing OxFord GB, Mar. 26, 2004, 112, 117-182.

Smyth et al., "Cytokines in Cancer Immunity and Immunotherapy", Immunological Reviews, Dec. 2004, 202(1), 275-293.

Stengaard-Pedersen et al. "Inherited Deficiency of Mannan-Binding Lectin-Associated Serine Protease 2", New England Journal of Medicine, Aug. 7, 2003, 349(6), 554-560.

Tony et al., "Design of Human Interleukin-4 Antagonists inhibiting Interleukin-4-dependent and Interleukin-13-dependent responses in T-cells and B-cells with high efficiency", European Journal of Biochemistry, Jun. 23, 1994, 225(2), 659-665.

Wang et al., "Structure of the Quaternary Complex of Interleukin-2 with it's A,B, and Yc Receptors", Science, Nov. 18, 2005, 310(5751), 1159-1163.

Wlodaver,A. et al., "Crystal Structure of Human Recombinant Interleukin-4 at 2.25 A Resolution", Febs Letters, Aug. 31, 1992, 309(1), 59-64.

Zalipsky "Chemistry of Polyethylene Glycol Conjugates with biologically active molecules", Advanced Drug Delivery Reviews, Sep. 1995, 16(2-3), 157-182.

Zhang et al., "Functional Epitope of Common Y Chain for Interleukin-4 Binding", European Journal of Biochemistry, Jan. 2002, 269(5), 1490-1499.

Zhang et al., "Human IL-21 and IL-4 bind to partially overlapping epitopes of Common Y-Chain", Biochemical and Biophysical Research Communications, Jan. 10, 2003, 300(2), 291-296.

Zhang et al., "Intratumoral T Cells, Recurrence, and Survival in Epithelial Ovarian Cancer", New England Journal of Medicine, Jan. 16, 2003, 348(3), 203-213.

* cited by examiner

|        |                                                          |     |
|--------|----------------------------------------------------------|-----|
| hIL21  | -QGQDRHMIRMRQLIDIVDQLKNYVND------LVPEFLPAPE-DVETNCEWSAFSCFQKAQ | 54  |
| hIL4   | ---HKCDITLQEIIKTLNSLTEQKT---LCTELTVTDIFAASKNTTEKETFCRAATVL    | 52  |
| hIL2   | ---STKKTQLQLEHLLLDLQMILNGINNYKNPKLTRMLTFKFYMPKK---ATELKHLQCLEEEL | 60  |

|        |                                                          |     |
|--------|----------------------------------------------------------|-----|
| hIL21  | LKS------ANTGNNERIINVSIKKLKRKPPSTNAGRRQKHRLTCPSCDSYEKKPPK | 105 |
| hIL4   | RQFYSHHEKDTRCLGATAQQFHRHKQLIRFLKRLDRNLWGLAG----LNSCPVKEANQSTLE | 110 |
| hIL2   | KPLEEVLN-----LAQSKNFHLRPRDLISNINVIVLELKGSETT----FMC-EYADETATIV | 112 |

|        |                                      |     |
|--------|--------------------------------------|-----|
| hIL21  | EFLERFKSLLQKMIHQHLSSRTHGSEDS          | 133 |
| hIL4   | NFLERLKTIMREKYSKCSS-------            | 129 |
| hIL2   | EFLNRWITFCQSIISTLT--------            | 130 |

FIGURE 3B

```
                                                                                                            56
                                                                                                            56
                                                                                                            55
                 9           19              29            39              48          56
hIL21R       ---WGCPDLVCYTDYLQTVI CI LEMWNLHPS-TLTLTWQDQYEELKDEATSCSLHRSA-HN
hIL4R        -FKVLQEPTCVSDYMSISTCEWKMNGPTNCSTELRLLYQLVFL-LSEAHTCIPENNGG--
hIL2R        AVQGTSQFTCFYNSRAQISCVWSQDGALQD-TSCQVHAWPDR--RRWQQTCELLPVSQ--

109
                                                                                                           104
                                                                                                           112
                63           68              78            84              94         104
hIL21R       ATHATYTCHMDVF-----HFMADDIFSVNITDQSG--NYSQECGSFLLAESIKPAPPFNV
hIL4R        ---AGCVCHLLMD----DVVSADNYTLDLWAG---QQLLWKGSFKPSEHVKPRAPGNL
hIL2R        ---ASWACNLILGAPDSQKLTTVDIVTLRVLCREGVRWRVMAIQDFKPFENRLMAPISL 167
                                                                                                           159
                                                                                                           167
               114          123             132           142             149         159
hIL21R       TVTFS--GQYNISWRSDYEDPAFYMLKGKLQYELQYRNRGDPWAVSPRRKLISVDSRSVS
hIL4R        TVHTNVSDTLLLTWSNPY-PPDNY-LYNHLTYAVNIWSENDP---ADFRIYNVTYLEPSL
hIL2R        QVVHVETHRCNISWEISQ--ASHY-FERHLEFEARTLSPGHTW--EEAPLLTLKQKQEWI 203
                                                                                                           207
                                                                                                           214
               169         179              186           196             206         207
hIL21R       LLPLEFRK-DSSYELQVRAGPMPGSSYQGTWSEWSDP-----KWHNSYREPFEQH
hIL4R        RIAASTLKSGISYRARVRAWAQA---YNTTWSEWSPSTKWHNSYREPFEQH
hIL2R        CLETLTP--DTQYEFQVRVKPLQGE-F-TTWSPWSQPLAFRTKPAALGKDT
```

INTERLEUKIN-21 VARIANTS WITH ALTERED BINDING TO THE IL-21 RECEPTOR

CROSS REFERENCE TO RELATED APPLICATIONS

This application is the National Stage Entry of International Application No. PCT/EP2007/064326, filed Dec. 20, 2007, which claims the benefit of European Patent Application No. 06126901.5, filed Dec. 21, 2006.

FIELD OF THE INVENTION

The invention is concerned with new IL-21 variants having an altered binding to the common gamma chain ($\gamma_c$) and the use thereof in therapy.

BACKGROUND OF THE INVENTION

Interleukin-21 (IL-21) is a recently identified type 1 cytokine, which is secreted as a 133-amino acid protein by activated CD4$^+$ T cells (Parrish-Novak, J. et al., Nature 408, 57-63 (2000)). The IL-21 cytokine has been demonstrated to possess potent stimulatory effects on the proliferation, differentiation and activation of several classes of haematopoietic cells including B-cells, T-cells and NK-cells. The biological effects of IL-21 are mediated via activation of the IL-21 receptor complex, which is composed of an IL-21 private receptor chain (IL-21Rα) in complex with the common gamma chain ($\gamma_c$), which similarly constitutes an essential component of the signalling receptor complex of the cytokines IL-2, IL-4, IL-7, IL-9, and IL-15. These cytokines thus constitute a subfamily referred to as common gamma chain cytokines, with IL-21 being the most recently added member.

Within the common gamma chain family of cytokines, high resolution structural information has been obtained through X-ray crystallography and NMR spectroscopy for IL-2 and IL-4 (Brandhuber, B. J. et al., Science 238, 1707-1709 (1987), Mott, H. R. et al., Journal of Molecular Biology 247, 979-994 (1995), Powers, R. et al., Science 256, 1673-1677 (1992), Wlodaver, A. et al., Febs Letters 309, 59-64 (1992). It is apparent from these studies that IL-2 and IL-4 along with other type 1 cytokines, including IL-1β, IL-2, IL-4, and GM-CSF, share a common overall topology in their structures in spite of a distant homology in primary sequence. The common structural motif of these proteins consists of a central four-helical bundle, arranged in an up-up-down-down topology, connected by loops which are characterized by a high degree of structural freedom, a considerable difference in loop length, and variation in the number, and positioning, of stabilizing disulfide bridges. In the IL-21 amino acid sequence as shown in SEQ ID No. 1 (a 162 aa long polypeptide), helix A is defined by amino acid residues 41-56; helix B by amino acid residues 69-84; helix C by amino acid residues 92-105; and helix D by amino acid residues 135-148.

Crystal structures have also been reported for IL-2 and IL-4 in complex with the corresponding private chains and, in the case of IL-2, the common gamma chain (Wang, X. Q. et al., Science 310, 1159-1163 (2005), Hage, T. et al., Cell 97, 271-281 (1999)). IL-2 is distinct from both IL-4 and IL-21 by having two private receptor chains, IL-2Rα and IL-2Rβ, where IL-2Rβ is homologous to IL-4Rα and IL-21Rα. Only minor structural differences are observed between the free and receptor bound forms of IL-2 and IL-4 indicating that only slight structural changes occur for these cytokines upon complex formation. These studies accurately identify the residues of the cytokines involved in receptor binding, and closely mirror earlier results obtained from mutagenesis studies.

IL-4 antagonists have been designed by making variants for which binding to $\gamma_c$ has been abolished while preserving binding to the private receptor chain. This was accomplished by a double mutation [R121D,Y124D] in helix D (Tony, H. P. et al., European Journal of Biochemistry 225, 659-665 (1994)). The IL-4 epitope for $\gamma_c$ binding have been further explored by biacore analyses with IL-4 variants (Zhang, J. L. et al., European Journal of Biochemistry 269, 1490-1499 (2002). Recently, it has been shown that IL-4 and IL-21 bind to partially overlapping epitopes of $\gamma_c$ (Zhang, J. L. et al., Biochemical and Biophysical Research Communications 300, 291-296 (2003)).

By analogy to the IL-4 antagonist ([R121D,Y124D]-IL-4), IL-21 variants with antagonistic properties have been generated by mutation of residues in helix D corresponding to R121 and Y124 in IL-4 (WO2003040313).

Both IL-21 agonism and antagonism have thus been implicated as a potentially useful mechanism for treating diseases and disorders. Generating IL-21 variants having modulated activity can be a useful tool in order to elucidate more about such diseases and disorders and may present potential targets for drug development. As such, there is a continuing need for IL-21-variants and a method for designing such.

SUMMARY OF THE INVENTION

The present invention concerns isolated IL-21 peptides having a mutation in one or more amino acid residues as compared to an IL-21 peptide having the amino acid sequence of SEQ ID No.2, wherein the activation mediated by said peptide through the IL-21 receptor is altered as compared to an IL-21 peptide having the amino acid sequence of SEQ ID No. 2.

The present invention concerns isolated IL-21 peptides having a mutation in one or more of the amino acid residues involved in the binding of IL-21 to the common gamma chain ($\gamma_c$) of the IL-21 receptor, wherein the activation mediated by said peptide through the IL-21 receptor is altered as compared to an IL-21 peptide having the amino acid sequence of SEQ ID No. 2.

The present invention concerns isolated IL-21 peptides having a mutation in one or more of the amino acid residues involved in the binding of IL-21 to the common gamma chain ($\gamma_c$) of the IL-21 receptor, wherein the IL-21 peptide has an altered binding to the IL-21 receptor as compared to an IL-21 peptide having the amino acid sequence of SEQ ID No. 2.

The present invention also concerns isolated IL-21 peptides having a mutation in one or more of the amino acid residues involved in the binding of IL-21 to the common gamma chain ($\gamma_c$) of the IL-21 receptor, wherein said IL-21 peptide has an altered binding to the $\gamma_c$ of the IL-21 receptor as compared to an IL-21 peptide having the amino acid sequence of SEQ ID No. 2.

The present invention also concerns pharmaceutical compositions comprising such peptides, as well as use of the peptides and/or said preparations in therapy.

The present invention also concerns the use of a peptide according to the present invention or a pharmaceutical composition according to the present invention, wherein the IL-21 peptide is an antagonist of the IL-21 receptor, for use in treating a disease or disorder, wherein said disease or disorder may be treatable by use of an IL-21 antagonist.

The present invention also concerns the use of a peptide according to the present invention, wherein the IL-21 peptide is an antagonist of the IL-21 receptor, for preparation of a pharmaceutical composition for treating a disease or disorder, wherein said disease or disorder may be treatable by use of an IL-21 antagonist.

The present invention also concerns methods for the treatment of a disease or disorder, wherein said disease or disorder may be treatable by use of an IL-21 antagonist, wherein said treatment comprises the administration of an effective amount of an IL-21 peptide according to the present invention, wherein said IL-21 peptide is an antagonist of the IL-21 receptor.

The present invention also concerns a use of a peptide according to the present invention, wherein the IL-21 peptide is an agonist of the IL-21 receptor, for use in treating a disease or disorder, wherein said disease or disorder may be treatable by use of an IL-21 agonist.

The present invention also concerns the use of a peptide according to the present invention, wherein the IL-21 peptide is an agonist of the IL-21 receptor, for preparation of a pharmaceutical composition for treating a disease or disorder, wherein said disease or disorder may be treatable by use of an IL-21 agonist.

The present invention also concerns methods for the treatment of a disease or disorder, wherein said disease or disorder may be treatable by use of an IL-21 agonist, wherein said treatment comprises the administration of an effective amount of a peptide according to the present invention, wherein said IL-21 peptide is an agonist of the IL-21 receptor, to a patient in need thereof.

The present invention also concerns an isolated nucleic acid construct encoding a peptide according to the present invention.

The present invention also concerns a host cell comprising a nucleic acid construct according to the present invention.

The present invention also concerns an antibody that specifically binds a peptide according to the present invention.

DESCRIPTION OF THE DRAWINGS

FIG. 3: (A) Sequence alignment of hIL-2, hIL-4 and hIL-21 based on a structural alignment and adjusted by hand. Numbering follows hIL-21. (B) Sequence alignment of hIL-2β, hIL-4Rα and hIL-21Rα. The alignment was done manually using a structural alignment of hIL-2β and hIL-4Rα as a starting point. Numbering follows hIL-21Rα.

DESCRIPTION OF THE SEQUENCES

Figure 1:
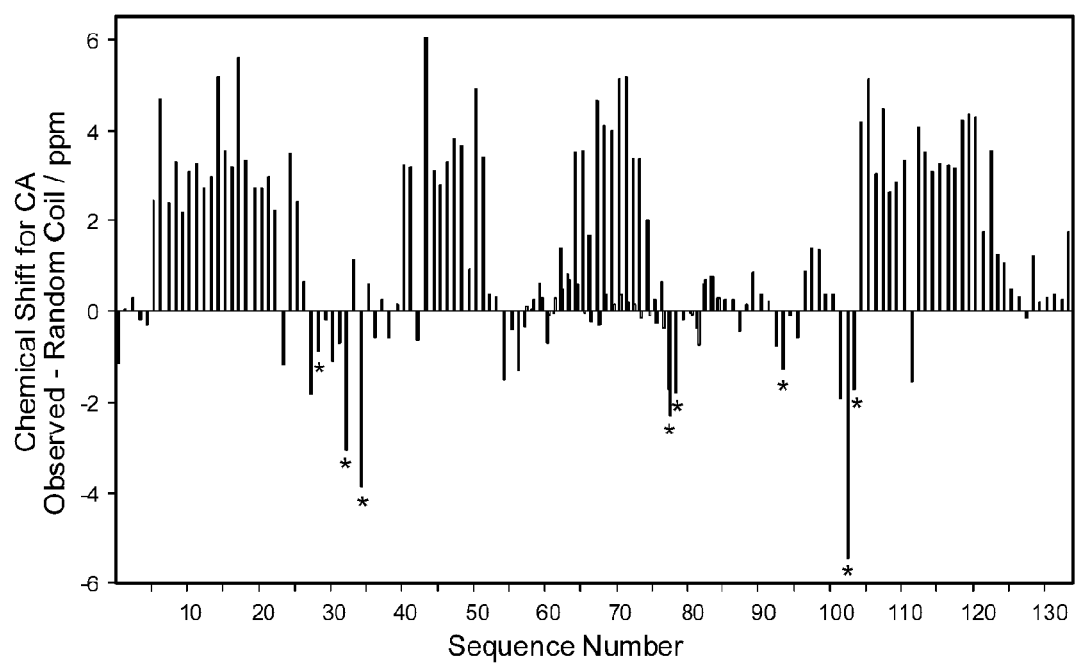
FIG. 1: Plot of difference between observed CA chemical shift values and tabulated chemical shift values for random coil against sequence number. For $Ser^{57}$ to $Gly^{84}$ the major and minor forms at 27° C. are shown in black and red, respectively. Asterisk marks residues preceding a proline.

SEQ ID No. 1: Amino acid sequence for full-length IL-21 (1-162 aa). In this sequence, helix A is defined by amino acid residues 36-55; helix B by amino acid residues 73-81; helix C by amino acid residues 88-102; and helix D by amino acid residues 133-153.

SEQ ID No. 2: Amino acid sequence for hIL-21 (residues 30-162 of SEQ ID No. 1). In this sequence, helix A is defined by amino acid residues 7-26; helix B by amino acid residues 44-52; helix C by amino acid residues 59-73; and helix D by amino acid residues 104-124.

SEQ ID No. 3: Amino acid sequence for Met-hIL-21 (SEQ ID No. 2 with an additional N-terminal methionine residue).

DESCRIPTION OF THE INVENTION

Activation of the IL-21 receptor complex proceeds via binding of IL-21 to the functional heterodimeric receptor complex composed by the two receptor subunits IL-21R and $\gamma_c$. Formation of the tertinary IL-21 receptor complex induces a reorientation of the intracellular receptor domains leading to activation of intracellular signal pathways. IL-21 antagonists may be generated by abolishment of binding between IL-21 and the $\gamma_c$, which for instance could be achieved by disruption of the IL-21 and $\gamma_c$ binding interface. Such IL-21 variants cannot activate the receptor complex and are at the same time highly specific antagonists as they still compete with native IL-21 for the IL-21R subunit. Such variants may be constructed by mutating IL-21 residues involved in $\gamma_c$ binding. The identity of these residues has hitherto been unknown. This invention identifies all residues in IL-21 that are important for the interaction between IL-21 and $\gamma_c$, and determines their importance for $\gamma_c$ binding by functional characterization of the corresponding individually alanine substituted IL-21 variants.

A high-resolution three-dimensional structure of Met-hIL-21 (SEQ ID No.3, which is fragment 30-162 of SEQ ID No. 1 with an additional N-terminal methionine) was resolved by heteronuclear NMR spectroscopy. Overall the Met-hIL-21 structure is dominated by a well-defined central four-helical bundle, arranged in an up-up-down-down topology, as observed for other cytokines. A 3D model of the complex between IL-21 and $\gamma_c$ was created based on the crystal structure of the IL-2/$\gamma_c$/IL-2Rα/IL-2Rβ receptor complex together with the NMR structure of Met-hIL-21. Residues of IL-21 involved in $\gamma_c$ binding were identified using the 3D model. For the set of residues in IL-21 involved in binding to $\gamma_c$, an alanine scan was carried out to determine the importance of individual residues for $\gamma_c$ binding.

Knowledge of these individual residues is used in the generation of variants of IL-21 having a modulated binding to $\gamma_c$. For example abolishment of binding to $\gamma_c$ may lead to the generation of IL-21 variants with antagonistic properties as mentioned above, while IL-21 variants with improved binding to $\gamma_c$ may lead to superactive IL-21 agonists.

The present invention concerns isolated IL-21 peptides having a mutation in one or more amino acid residues as compared to an IL-21 peptide having the amino acid sequence of SEQ ID No.2, wherein the activation mediated by said peptide through the IL-21 receptor is altered as compared to an IL-21 peptide having the amino acid sequence of SEQ ID No. 2.

The present invention also concerns an isolated IL-21 peptide having a mutation in one or more of the amino acid residues involved in the binding of IL-21 to the common gamma chain ($\gamma_c$) of the IL-21 receptor, wherein the activation mediated by said peptide through the IL-21 receptor is altered as compared to an IL-21 peptide having the amino acid sequence of SEQ ID No. 2.

The activation mediated by said peptide may for instance be determined by use of Assay (Ia) or (Ib) herein.

In one embodiment, the invention relates to an isolated IL-21 peptide having a mutation in one or more of the amino acid residues involved in the binding of IL-21 to the common gamma chain ($\gamma_c$) of the IL-21 receptor, wherein the IL-21 peptide has an altered binding to the IL-21 receptor as compared to an IL-21 peptide having the amino acid sequence of SEQ ID No. 2. The binding to the IL-21 peptide to the IL-21 receptor may for instance be determined by use of Assay (II) as described herein or may be measured indirectly by measuring the activivation as described in Assays (Ia) and (Ib).

In one embodiment, the invention relates to an isolated IL-21 peptide having a mutation in one or more of the amino acid residues involved in the binding of IL-21 to the common gamma chain ($\gamma_c$) of the IL-21 receptor, wherein said IL-21 peptide has an altered binding to the $\gamma_c$ of the IL-21 receptor as compared to an IL-21 peptide having the amino acid sequence of SEQ ID No. 2.

The binding to the IL-21 peptide to the IL-21 receptor or the common gamma chain ($\gamma_c$) may for instance be determined by use of Assay (II) as described herein.

The term peptide includes any suitable peptide and may be used synonymously with the terms polypeptide and protein, unless otherwise stated or contradicted by context; provided that the reader recognize that each type of respective amino acid polymer-containing molecule may be associated with significant differences and thereby form individual embodiments of the present invention (for example, a peptide such as an antibody, which is composed of multiple polypeptide chains, is significantly different from, for example, a single chain antibody, a peptide immunoadhesin, or single chain immunogenic peptide). Therefore, the term peptide herein should generally be understood as referring to any suitable peptide of any suitable size and composition (with respect to the number of amino acids and number of associated chains in a protein molecule). Moreover, peptides in the context of the inventive methods and compositions described herein may comprise non-naturally occurring and/or non-L amino acid residues, unless otherwise stated or contradicted by context.

The term peptide, unless otherwise stated or contradicted by context, (and if discussed as individual embodiments of the term(s) polypeptide and/or protein) also encompasses derivatized peptide molecules. Briefly, in the context of the present invention, a derivative is a peptide in which one or more of the amino acid residues of the peptide have been chemically modified (for instance by alkylation, acylation, ester formation, or amide formation) or associated with one or more non-amino acid organic and/or inorganic atomic or molecular substituents (for instance a polyethylene glycol (PEG) group, a lipophilic substituent (which optionally may be linked to the amino acid sequence of the peptide by a spacer residue or group such as β-alanine, γ-aminobutyric acid (GABA), L/D-glutamic acid, succinic acid, and the like), a fluorophore, biotin, a radionuclide, etc.) and may also or alternatively comprise non-essential, non-naturally occurring, and/or non-L amino acid residues, unless otherwise stated or contradicted by context (however, it should again be recognized that such derivatives may, in and of themselves, be considered independent features of the present invention and inclusion of such molecules within the meaning of peptide is done for the sake of convenience in describing the present invention rather than to imply any sort of equivalence between naked peptides and such derivatives). Non-limiting examples of such amino acid residues include for instance 2-aminoadipic acid, 3-amino-adipic acid, β-alanine, β-aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-di-aminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methyl-isoleucine, 6-N-methyllysine, N-methylvaline, norvaline, norleucine, ornithine, and statine halogenated amino acids.

IL-21 peptides refers to any peptide that specifically binds to the IL-21 receptor under cellular and/or physiological conditions for an amount of time sufficient to induce, promote, enhance, and/or otherwise modulate a physiological effect associated with the antigen; to allow detection by ELISA, Western blot, or other similarly suitable protein binding technique described herein and/or known in the art and/or to otherwise be detectably bound thereto after a relevant period of time (for instance at least about 15 minutes, at least about 30 minutes, at least about 45 minutes, at least about 1 hour, at least about 2 hours, at least about 4 hours, at least about 6 hours, at least about 12 hours, about 1-24 hours, about 1-36 hours, about 1-48 hours, about 1-72 hours, about one week, or longer). The binding of the IL-21 peptide to the IL-21 receptor may for instance be determined by use of Assay (II) as described herein or may be measured indirectly by measuring the activivation as described in Assays (Ia) and (Ib).

In one embodiment, a IL-21 peptide according to the present invention is an analogue of human IL-21.

The term "analogue" as used herein referring to a polypeptide means a modified peptide wherein one or more amino acid residues of the peptide have been substituted by other amino acid residues and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide and/or in-chain. All amino acids for which the optical isomer is not stated are to be understood to mean the L-isomer.

The term "IL-21 analogue" or "analogue of IL-21" or "analogue of human IL-21" as used herein referring to an analogue of IL-21 (or human IL-21), which has the capability of binding to the IL-21 receptor and in particular to the common gamma chain ($\gamma_c$) of the IL-21 receptor.

In one embodiment, an IL-21 peptide of the invention has an amino acid sequence having at least 80% identity to SEQ ID No. 1 or SEQ ID No. 2. In one embodiment, an IL-21 peptide of the invention has an amino acid sequence having at least 85%, such as at least 90%, for instance at least 95%, such as for instance at least 99% identity to SEQ ID No. 1 or SEQ ID No. 2.

The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two peptides for which the percent sequence identity is to be determined are aligned for optimal matching of their respective amino acids (the "matched span", as determined by the algorithm). A gap opening penalty (which is calculated as 3 times, the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., Proc. Natl. Acad. Sci. USA 89, 10915-10919 (1992) for the BLOSUM 62 comparison matrix) is also used by the algorithm.

Preferred parameters for a peptide sequence comparison include the following:

Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

In one embodiment, an IL-21 peptide of the invention has an amino acid sequence, which sequence is at least 80% similar to SEQ ID No. 1 or SEQ ID No. 2. In one embodiment, an IL-21 peptide of the invention has an amino acid sequence, which sequence is at least 85%, such as at least 90%, for instance at least 95%, such as for instance at least 99% identity to SEQ ID No. 1 or SEQ ID No. 2.

The term "similarity" is a concept related to identity, but in contrast to "identity", refers to a sequence relationship that includes both identical matches and conservative substitution matches. If two polypeptide sequences have, for example, (fraction (10/20)) identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% ((fraction (15/20))). Therefore, in cases where there are conservative substitutions, the degree of similarity between two polypeptides will be higher than the percent identity between those two polypeptides.

Conservative modifications a peptide comprising an amino acid sequence of SEQ ID No. 1 or SEQ ID No. 2 (and the corresponding modifications to the encoding nucleic acids) will produce peptides having functional and chemical characteristics similar to those of a peptide comprising an amino acid sequence of SEQ ID No. 1 or SEQ ID No. 2. In contrast, substantial modifications in the functional and/or chemical characteristics of peptides according to the invention as compared to a peptide comprising an amino acid sequence of SEQ ID No. 1 or SEQ ID No. 2 may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., Acta Physiol. Scand. Suppl. 643, 55-67 (1998); Sasaki et al., Adv. Biophys. 35, 1-24 (1998), which discuss alanine scanning mutagenesis).

Desired amino acid substitutions (whether conservative or non-conservative) may be determined by those skilled in the art at the time such substitutions are desired. For example, amino acid substitutions can be used to identify important residues of the peptides according to the invention, or to increase or decrease the affinity of the peptides described herein for the receptor in addition to the already described mutations.

Naturally occurring residues may be divided into classes based on common side chain properties:
1) hydrophobic: norleucine, Met, Ala, Val, Leu, Iie;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157, 105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those that are within ±1 are particularly preferred, and those within ±0.5 are even more particularly preferred.

It is also understood in the art that the substitution of like amino acids may be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine ('3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those that are within ±1 are particularly preferred, and those within ±0.5 are even more particularly preferred. One may also identify epitopes from primary amino acid sequences on the basis of hydrophilicity. These regions are also referred to as "epitopic core regions.".

Peptides of the present invention may also include non-naturally occurring amino acids.

In one embodiment, the activation of said peptide mediated through the IL-21 receptor is decreased as compared to an IL-21 peptide having the amino acid sequence of SEQ ID No. 2. In one embodiment, the decrease in the binding of said peptide to the IL-21 receptor is at least 2-fold, such as at least 5-fold, for instance at least 10-fold, such as at least 20-fold, for instance at least 50-fold, such as at least 100-fold, for instance at least 500-fold, such as at least 1000-fold as compared to the binding of a IL-21 peptide having the amino acid sequence of SEQ ID No. 2 to the IL-21 receptor.

In one embodiment, the activation of said peptide mediated through the IL-21 receptor is increased as compared to an IL-21 peptide having the amino acid sequence of SEQ ID No. 2. In one embodiment, the increase in the binding of said peptide to the IL-21 receptor is at least 2-fold, such as at least 5-fold, for instance at least 10-fold, such as at least 20-fold, for instance at least 50-fold as compared to the binding of a IL-21 peptide having the amino acid sequence of SEQ ID No. 2 to the IL-21 receptor.

The decrease or increase in activation through the receptor may be determined by use of for instance the assays described herein as Assay (Ia) or (Ib).

In one embodiment, an IL-21 peptide according to the invention is an antagonist of the IL-21 receptor. In this specification, an antagonist may be a partial agonist or a full antagonist meaning IL-21 peptides that produce either a less efficacious activation or no measurable activation, respectively, when analyzed using Assay (Ia) or (Ib). A less efficacious activation meaning activation corresponding to less than 50% of that achieved at the corresponding dose of the natural agonist, hIL-21. In addition, an antagonist must produce inhibition of the receptor activation mediated by the natural agonist hIL-21 when the former is present at a concentration of 1 nM or less.

In one embodiment, the introduction of the mutation(s) according to the invention is responsible for or contributory to the antagonistic activity of the IL-21 peptide.

In one embodiment, an IL-21 peptide according to the invention is an agonist of the IL-21 receptor. For the purposes of this specification, an agonist of IL-21 is a molecule, which activates the IL-21 receptor in an assay such as Assay (Ia) or (Ib) as described herein.

In one embodiment, an IL-21 peptide according to the invention carries one or more antagonistic mutations in the region corresponding to Helix D of SEQ ID No. 1 as described in for instance Brandt, C et al., Journal of Leukocyte Biology Suppl. S 119, 46-46 (2001). In one embodiment, one or more of said antagonistic mutations in Helix D is a mutation in one or more of the amino acid residues corresponding to positions Gln-116 and Ile-119 in SEQ ID No. 2, as described in WO2003040313. In one embodiment, Gln-116 has been substituted with an Asp. In one embodiment, Ile-119 has been substituted with an Asp. In one embodiment, the amino acid residues corresponding to positions Ile-119 to Ser-133 has been deleted, also as described in WO2003040313.

In one embodiment, an IL-21 peptide according to the invention carries one or of the mutations as described in CN1513993A. In one embodiment, one or more of said mutations is a mutation in one or more of the amino acid residues corresponding to positions Lys-21, Ala-83 and Leu-123 in SEQ ID No. 2. In one embodiment, Lys-21 has been substituted with a His. In one embodiment, Ala-83 has been substituted with a Gly. In one embodiment, Leu-123 has been substituted with an Ile. In one embodiment, Lys-21 has been substituted with a His, Ala-83 has been substituted with a Gly, and Leu-123 has been substituted with an Ile.

In one embodiment, an IL-21 peptide according to the invention carries one or of the mutations as described in WO2004112703.

In one embodiment, said peptide carries one or more of the mutations as described in WO2004112703. In one embodiment, said agonistic IL-21 peptide has a sequence, wherein one or more of the amino acids in the region corresponding to amino acid residue 65 to 96 in SEQ ID No. 2 has been deleted or substituted as described in International Patent Application PCT2006EP061635. In one embodiment, one or more of the amino acids in the region corresponding to amino acid residue 83 to 86 in SEQ ID No. 2 has been deleted or substituted. In one embodiment, one or more of the amino acids in the region corresponding to amino acid residue 83 to 88 in SEQ ID No. 2 has been deleted or substituted. In one embodiment, one or more of the amino acids in the region corresponding to amino acid residue 83 to 90 in SEQ ID No. 2 has been deleted or substituted. In one embodiment, one or more of the amino acids in the region corresponding to amino acid residue 82 to 88 in SEQ ID No. 2 has been deleted or substituted. In one embodiment, one or more of the amino acids in the region corresponding to amino acid residue 77 to 92 in SEQ ID No. 2 has been deleted or substituted. In one embodiment, one or more of the amino acids in the region corresponding to amino acid residue 71 to 92 in SEQ ID No. 2 has been deleted or substituted. In one embodiment, one or more of the amino acids in the region corresponding to amino acid residue 65 to 92 in SEQ ID No. 2 has been deleted or substituted. In one embodiment, one or more of the amino acids in the region corresponding to amino acid residue 77 to 96 in SEQ ID No. 2 has been deleted or substituted. In one embodiment, one or more of the amino acids in the region corresponding to amino acid residue 83 to 86 in SEQ ID No. 2 has been deleted or substituted. In one embodiment, one or more of the amino acids in the region corresponding to amino acid residue 83 to 88 in SEQ ID No. 2 has been deleted or substituted. In one embodiment, one or more of the amino acids in the region corresponding to amino acid residue 83 to 90 in SEQ ID No. 2 has been deleted or substituted. In one embodiment, one or more of the amino acids in the region corresponding to amino acid residue 82 to 88 in SEQ ID No. 2 has been deleted or substituted. In one embodiment, one or more of the amino acids in the region corresponding to amino acid residue 77 to 92 in SEQ ID No. 2 has been deleted or substituted. In one embodiment, one or more of the amino acids in the region corresponding to amino acid residue 71 to 92 in SEQ ID No. 2 has been deleted or substituted. In one embodiment, one or more of the amino acids in the region corresponding to amino acid residue 65 to 92 in SEQ ID No. 2 has been deleted or substituted. In one embodiment, one or more of the amino acids in the region corresponding to amino acid residue 77 to 96 in SEQ ID No. 2 has been deleted or substituted.

The modulation of binding to the common gamma chain ($\gamma_c$) of the IL-21 receptor may for instance be achieved by mutating one or more amino acid residues as described below.

In one embodiment, an IL-21 peptide according to the invention has a mutation in one or more of the amino acid residues corresponding to Met-7, Arg-11, Ile-14, Asp-18, Glu-36, Asp-37, Thr-40, Glu-100, Glu-109 Ser-113, Gln-116, Lys-117, Ile-119, His-120, Lys-123, Ser-125, Arg-126, Thr-127, His-128, Gly-129, Ser-130, Glu-131, Asp-132, and Ser-133 in SEQ ID No. 2.

In one embodiment, an IL-21 peptide according to the invention has a mutation in one or more of the amino acid residues corresponding to Met-7, Arg-11, Ile-14, Asp-18, Glu-100, Glu-109, Ser-113, Gln-116, Lys-117, Ile-119, His-120, and Leu-123 in SEQ ID No. 2.

In one embodiment, an IL-21 peptide according to the invention has a mutation in one or more of the amino acid residues corresponding to Met-7, Arg-11, Ile-14, Asp-18, Glu-36, Asp-37, Thr-40, Glu-100, Ser-125, Arg-126, Thr-127, His-128, Gly-129, Ser-130, Glu-131, Asp-132, and Ser-133 in SEQ ID No. 2.

In one embodiment, an IL-21 peptide according to the invention has a mutation in one or more of the amino acid residues corresponding to Arg-11, Glu-36, Asp-37, Thr-40, Glu-100, Ser-113, Lys-117, and His-120 in SEQ ID No. 2.

In one embodiment, an IL-21 peptide according to the invention has a mutation in one or more of the amino acid residues corresponding to Ile-14, Gln-116, and Lys-117 in SEQ ID No. 2.

In one embodiment, said peptide comprises a mutation in one or more of the amino acid residues in the region corresponding to Helix A in SEQ ID No. 1. In one embodiment, said peptide comprises a mutation in one or more of the amino acid residues corresponding to positions Met-7, Arg-11, Ile-14 and Asp-18.

In one embodiment, said peptide comprises a mutation in one or more of the amino acid residues in the region corresponding to loop NB in SEQ ID No. 1. For the purpose of this specification, loop A/B consists of amino acid residues 56 to 72 in SEQ ID No. 1, corresponding to amino acid residues 27 to 43 in SEQ ID No. 2. In one embodiment, said peptide comprises a mutation in one or more of the amino acid residues corresponding to positions Glu-36, Asp-37 and Thr-40 in SEQ ID No. 2.

In one embodiment, said peptide comprises a mutation in one or more of the amino acid residues in the region corresponding to loop C/D in SEQ ID No. 1. For the purpose of this specification, loop C/D consists of amino acid residues 103 to 132 in SEQ ID No. 1, corresponding to amino acid residues 74 to 103 in SEQ ID No. 2. In one embodiment, said peptide comprises a mutation in position Glu-100 in SEQ ID No. 2.

In one embodiment, said peptide comprises a mutation in one or more of the amino acid residues in the region corresponding to Helix D in SEQ ID No. 1. In one embodiment, said peptide comprises a mutation in one or more of the amino acid residues corresponding to positions Glu-109 Ser-113, Gln-116, Lys-117, Ile-119, His-120, and Lys-123 in SEQ ID No. 2.

In one embodiment, said peptide comprises a mutation in one or more of the amino acid residues in the ten most C-terminal amino acid residues. In one embodiment, said peptide comprises a mutation in one or more of the amino acid residues corresponding to positions Ser-125, Arg-126, Thr-127, His-128, Gly-129, Ser-130, Glu-131, Asp-132, and Ser-133 in SEQ ID No. 2.

In one embodiment, the mutation in the stated position is a substitution with Ala.

The peptides of the present invention may be prepared in different ways. The peptides may be prepared by protein synthetic methods known in the art. Due to the size of the peptides, this may be done more conveniently by synthesising several fragments of the peptides which are then combined to provide the peptides of the present invention. In a particular embodiment, however, the peptides of the present invention are prepared by fermentation of a suitable host comprising a nucleuic acid construct encoding the peptides of the present invention. This is well-known by a person skilled in the art.

Peptides according to the present invention may be used in the treatment of different diseases and disorders, where a modulation (such as increasing or a decreasing) IL-21 activity may prove beneficial for the patient. Peptides according to the present invention may be IL-21 agonists or IL-21 antagonists and as such may be useful for treating different diseases and disorders.

The present invention thus provides a peptide according to the present invention for use in therapy.

The present invention also provides the use of a peptide according to the present invention for use in therapy.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active peptides to prevent the onset of the symptoms or complications. The patient to be treated may be a mammal, in particular a human being, but it may also include animals, such as dogs, cats, cows, sheep and pigs. It is to be understood, that therapeutic and prophylactic (preventive) regimes represent separate aspects of the present invention.

A "therapeutically effective amount" of a peptide as used herein means an amount sufficient to cure, alleviate or partially arrest the clinical manifestations of a given disease and its complications. An amount adequate to accomplish this is defined as "therapeutically effective amount". Effective amounts for each purpose will depend on the type and severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

Peptides and pharmaceutical compositions according to the present invention, which peptides are IL-21 antagonists may be used in the treatment of a number of diseases and disorders.

Consequently, the present invention also provides the use of a peptide according to the present invention, wherein the IL-21 peptide is an antagonist of the IL-21 receptor, for use in treating a disease or disorder, wherein said disease or disorder may be treatable by use of an IL-21 antagonist. The present invention also provides the use of a peptide according to the present invention, wherein the IL-21 peptide is an antagonist of the IL-21 receptor, for the preparation of a pharmaceutical composition for treating a disease or disorder, wherein said disease or disorder may be treatable by use of an IL-21 antagonist. The present invention also provides a method for the treatment of a disease or disorder, wherein said disease or disorder may be treatable by use of an IL-21 antagonist, wherein said treatment comprises the administration of an effective amount of a peptide according to the present invention, wherein said IL-21 peptide is an antagonist of the IL-21 receptor, to a patient in need thereof.

In one embodiment, such disease or disorder is an autoimmune and/or inflammatory disease. Examples of such autoimmune and/or inflammatory diseases are Systemic Lupus Erythematosus (SLE), Rheumatoid Arthritis (RA) and inflammatory bowel disease (IBD) (including ulcerative colitis (UC) and Crohn's disease (CD)), multiple sclerosis (MS), scleroderma and type 1 diabetes (T1 D), and other diseases and disorders, such as PV (pemphigus vulgaris), psoriasis, atopic dermatitis, celiac disease, kol, hashimoto's thyroiditis graves' disease (thyroid), sjogren's syndrome, guillain-barre syndrome, goodpasture's syndrome, additon's disease, wegener's granulomatosis, primary biliary sclerosis, sclerosing cholangitis, autoimmune hepatitis, polymyalgia rheumatica, paynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia greata, and vitilgo. Other examples can be found in PCT application WO01/46420, which is directed at the use of IL-17 for treatment of autoimmune and/or inflammatory diseases and wherein several examples of such diseases are given.

In one embodiment, such disease or disorder is SLE, RA or IBD.

In one embodiment, such disease or disorder is MS.

Peptides and pharmaceutical compositions according to the present invention, which peptides are IL-21 agonists may be used in the treatment of a number of diseases and disorders Consequently, the present invention also provides the use of a peptide according to the present invention, wherein the IL-21 peptide is an agonist of the IL-21 receptor, for use in treating a disease or disorder, wherein said disease or disorder may be treatable by use of an IL-21 agonist. The present invention also provides the use of a peptide according to the present invention, wherein the IL-21 peptide is an agonist of the IL-21 receptor, for the preparation of a pharmaceutical composition for treating a disease or disorder, wherein said disease or disorder may be treatable by use of an IL-21 agonist. The present invention also provides a method for the treatment of a disease or disorder, wherein said disease or disorder may be treatable by use of an IL-21 agonist, wherein said treatment comprises the administration of an effective amount of a peptide according to the present invention, wherein said IL-21 peptide is an agonist of the IL-21 receptor, to a patient in need thereof.

In one embodiment, the disease or disorder is a cancer. In one embodiment, such cancer is selected from non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin. In one embodiment, said cancer is malignant melanoma.

The IL-21 peptides of the present invention may be administered in combination with other medicaments as is known in the art.

With regard to antagonistic IL-21 peptides and the treatment of autoimmune diseases, such combination therapy may include administration of an IL-21 peptide of the present invention together with a medicament, which together with the IL-21 peptide comprise an effective amount for preventing or treating such autoimmune diseases. Where said autoimmune disease is Type 1 diabetes, the combination therapy may encompass one or more of an agent that promotes the growth of pancreatic beta-cells or enhances beta-cell transplantation, such as beta cell growth or survival factors or immunomodulatory antibodies. Where said autoimmune disease is rheumatoid arthritis, said combination therapy may encompass one or more of methotrexate, an anti-TNF-α antibody, aTNF-α receptor-Ig fusion protein, an anti-IL-15 antibody, a non-steroidal anti-inflammatory drug (NSAID), or a disease-modifying anti-rheumatic drug (DMARD). For example, the additional agent may be a biological agent such as an anti-TNF agent (e.g., Enbrel®), infliximab (Remicade®) and adalimumab (Humira®) or rituximab (Rituxan®). Where said autoimmune disease is hematopoietic transplant rejection, hematopoietic growth factor(s) (such as erythropoietin, G-CSF, GM-CSF, IL-3, IL-11, thrombopoietin, etc.) or antimicrobial(s) (such as antibiotic, antiviral, antifungal drugs) may be administered. Where said autoimmune disease is psoriasis, the additional agent may be one or more of tar and derivatives thereof, phototherapy, corticosteroids, Cyclosporine A, vitamin D analogs, methotrexate, p38 mitogen-activated protein kinase (MAPK) inhibitors, as well as biologic agents such as anti-TNF-α agents and Rituxan®. Where said autoimmune disease is an inflammatory bowel disease (IBD) such as, for example, Crohn's Disease or ulcerative colitis, the additional agent may be one or more of aminosalicylates, corticosteroids, immunomodulators, antibiotics, or biologic agents such as Remicade® and Humira®.

With regard to agonistic IL-21 peptides and the treatment of cancers, such combination therapy may include administration of an IL-21 peptide of the present invention together with a medicament useful for treating cancer such as conventional chemotherapeutic agents, such as anti-metabolites (such as azathioprine, cytarabine, fludarabine phosphate, fludarabine, gemcitabine, cytarabine, cladribine, capecitabine 6-mercaptopurine, 6-thioguanine, methotrexate, 5-fluorouracil, and hydroxyurea) alkylating agents (such as melphalan, busulfan, cis-platin, carboplatin, cyclophosphamide, ifosphamide, dacarbazine, procarbazine, chlorambucil, thiotepa, lomustine, temozolamide) anti-mitotic agents (such as vinorelbine, vincristine, vinblastine, docetaxel, paclitaxel) topoisomerase inhibitors (such as doxorubicin, amsacrine, irinotecan, daunorubicin, epirubicin, mitomycin, mitoxantrone, idarubicin, teniposide, etoposide, topotecan) antibiotics (such as actinomycin and bleomycin) asparaginase, or the anthracyclines or the taxanes;

certain monoclonal antibodies (mAbs), such as Rituximab, Alemtuzumab, Trastuzumab, Gemtuzumab, Gemtuzumab-ozogamicin (Myelotarg®, Wyeth) Cetuximab (Erbitux™), Bevacizumab, HuMax-CD20, HuMax-EGFr, Zamyl and Pertuzumab and/or such as an antibody against tissue factor, killer Ig-like receptors (KIR), laminin-5, EGF-R, VEGF-R, PDGF-R, HER-2/neu, or an antibody against a tumor antigen such as PSA, PSCA, CEA, CA125, KSA, etc.;

cell cycle control/apoptosis regulators, such as compounds, which target regulators such as (i) cdc-25, (ii) cyclin-dependent kinases that overstimulate the cell cycle (for instance flavopiridol (L868275, HMR1275; Aventis), 7-hydroxystaurosporine (UCN-01, KW-2401; Kyowa Hakko Kogyo) and roscovitine (R-roscovitine, CYC202; Cyclacel)), and (iii) telomerase (such as BIBR1532 and SOT-095, as well as drugs that interfere with apoptotic pathways such as TNF-related apoptosis-inducing ligand (TRAIL)/apoptosis-2 ligand (Apo-2L), antibodies that activate TRAIL receptors, IFNα and anti-sense Bcl-2;

growth factor inhibitors, such as antibodies directed at the extracellular ligand binding domain of receptors of the epidermal growth factor receptor (EGF-R) family, and low molecular weight molecules that inhibit the tyrosine kinase domains of these receptors, for instance Herceptin, cetuximab, Tarceva and Iressa;

inhibitors of tumor vascularisation (anti-angiogenesis drugs and anti-metastatic agents) such as endostatin, angiostatin, antibodies that block factors that initiate angiogenesis (for instance anti-VEGF—Avastin), and low molecular compounds that inhibit angiogenesis by inhibiting key elements in relevant signal transduction pathways;

anti-angiogenesis drugs, such as avastin, neovastat, thalidomide, PTK787, ZK222584, ZD-6474, SU6668, PD547, 632, VEGF-Trap, CEP-7055, NM-3, SU11248 hormonal agents, such as estramustine phosphate, polyestradiol phosphate, estradiol, anastrozole, exemestane, letrozole, tamoxi-fen, megestrol acetate, medroxyprogesterone acetate, octreotide, cyproterone acetate, bi-caltumide, flutamide, tritorelin, leuprorelin, buserelin or goserelin;

agents that enhance the immune response against tumor cells or virus-infected cells, such as adjuvants, for instance vaccine adjuvants such as QS21, GM-CSF and CpG oligodeoxynucleotides, lipopolysaccharide, polyinosinic:polycytidylic acid, α-galctosylceramide or analogues thereof, histamine dihydrochloride, or aluminum hydroxide;

cytokines, such as IFN-α, IFN-β IFNγ, IL-2, PEG-IL-2, IL-4, IL-6, IL-7, IL-12, IL-13, IL-15, IL-18, IL-23, IL-27, IL-28a, IL-28b, IL-29, GM-CSF, Flt3 ligand or stem cell factor or an analogue or derivative of any of these;

cisplatin, tamoxifen, DTIC, carmustine, carboplatin, vinblastine, vindesine, thymosin-α, autologous LAK cells, gemcitabine;

agents that block inhibitory signalling in the immune system, such as mAbs specific for CTLA-4 (anti-CTLA-4), mAbs specific for KIR (anti-KIR), mAbs specific for LIR (anti-LIR), mAbs specific for CD94 (anti-CD94), or mAbs specific for NKG2A (anti-NKG2A);

anti-anergic agents, such as MDX-010 (Phan et al. Proc. Natl. Acad. Sci. USA 100, 8372 (2003));

antibodies against an inhibitory receptor expressed on an NK cell, a T cell or a NKT cell;

therapeutic vaccines;

agents that interfere with tumor growth, metastasis or spread of virus-infected cells; and immunosuppressive/immunomodulatory agents such as agents with influence on T-lymphocyte homing for instance FTY-720, calcineurin inhibitors such as valspodar, PSC 833, TOR-inhibitors, sirolimus, everolimus and rapmycin.

Such combination therapy may also include administration of an IL-21 peptide of the present invention together with radiotherapy, such as external beam radiation therapy (EBRT) or internal radiotherapy (brachytherapy (BT)), typical radioactive atoms that have been used include radium, Cesium-137, Iridium-192, Americium-241, Gold-198, Cobalt-57, Copper-67, Technetium-99, Iodide-123, Iodide-131 and Indium-111

Such combination therapy may also include administration of an IL-21 peptide of the present invention together with cellular immunotherapy, which may include isolation of cells that can stimulate or exert an anti-cancer response from patients, expanding these into larger numbers, and reintroducing them into the same or another patient.

Such combination therapy may also include administration of an IL-21 peptide of the present invention together with internal vaccination, which refers to drug- or radiation-induced cell death of tumor cells that leads to elicitation of an immune response directed towards (i) said tumor cells as a whole or (ii) parts of said tumor cells including (a) secreted proteins, glycoproteins or other products, (b) membrane-associated proteins or glycoproteins or other components associated with or inserted in membranes and (c) intracellular proteins or other intracellular components.

Such combination therapy may also include administration of an IL-21 peptide of the present invention together with gene therapy, which includes transfer of genetic material into a cell to transiently or permanently alter the cellular phenotype.

Such combination treatments with IL-21 is also described in International Patent Applications PCT2006EP061635, WO2003103589, WO2005/037306 and WO2005113001.

The combination treatment may be carried out in any way as deemed necessary or convenient by the person skilled in the art and for the purpose of this specification, no limitations with regard to the order, amount, repetition or relative amount of the compounds to be used in combination is contemplated.

Accordingly, the IL-21 peptides according to the present invention for use in therapy may be formulated into pharmaceutical compositions. The present invention is also related to pharmaceutical compositions comprising peptides according to the present invention. Pharmaceutical compositions according to the present invention may be administered alone or in combination with pharmaceutically acceptable carriers or excipients, in either single or multiple doses. The formulation of the combination may be as one dose unit combining the compounds, or they may be formulated as separate doses. The pharmaceutical compositions comprising IL-21 variants according to the present invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions or suspensions.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen. The route of administration may be any route, which effectively transports the active compound to the appropriate or desired site of action.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, crémes, gels, inhalants, dermal patches, implants etc.

A typical oral dosage is in the range of from about 0.001 to about 100 mg/kg body weight per day, such as from about 0.01 to about 50 mg/kg body weight per day, for example from about 0.05 to about 10 mg/kg body weight per day administered in one or more dosages such as 1 to 3 dosages. The exact dosage will depend upon the nature of the IL-21 polypeptide chosen, the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, for example from about 0.1 to about 500 mg, such as from about 0.5 mg to about 200 mg.

For parenteral routes such as intravenous, intrathecal, intramuscular and similar administration, typically doses are in the order of about half the dose employed for oral administration.

Salts of IL-21 variants according to the present invention are especially relevant when the peptide is in solid or crystalline form For parenteral administration, solutions of the IL-21 variants according to the present invention in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining a IL-21 variant according to the present invention and the pharmaceutically acceptable carriers are then readily administered in a variety of dosage forms suitable for the disclosed routes of administration. The formulations may conveniently be presented in unit dosage form by methods known in the art of pharmacy.

For nasal administration, the preparation may contain a IL-21 variant according to the present invention dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Formulations of IL-21 variants according to the present invention, optionally together with the combination agent suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsules wherein the active ingredient is mixed with water or an oil medium, for example peanut oil, liquid paraffin, or olive oil.

Aqueous suspensions may contain the IL-21 variants according to the present invention, optionally together with the combination agent in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions of IL-21 variants according to the present invention, optionally together with the combination agent may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservatives and flavouring and colouring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The IL-21 variants according to the present invention, optionally together with the combination agent may also be administered in the form of liposome delivery systems, such as small unilamellar vesicles, large unilamellar vesicles, and multilamellar vesicles. Liposomes may be formed from a variety of phospholipids, such as cholesterol, stearyl-amine, or phosphatidylcholines.

In addition, some of the IL-21 variants according to the present invention may form solvates with water or common organic solvents. Such solvates are also encompassed within the scope of the invention.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

The IL-21 variants according to the present invention, optionally together with the combination agent may be administered to a mammal, especially a human, in need of such treatment. Such mammals include also animals, both domestic animals, e.g. household pets, and non-domestic animals such as wildlife.

Pharmaceutical compositions containing a IL-21 variant according to the present invention may be administered one or more times per day or week, for instance at mealtimes. An effective amount of such a pharmaceutical composition is the amount that provides a clinically significant effect. Such amounts will depend, in part, on the particular condition to be treated, age, weight, and general health of the patient, and other factors evident to those skilled in the art.

The present invention also provides an isolated nucleic acid construct encoding a peptide according to the present invention.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a peptide of interest. The construct may optionally contain other nucleic acid segments.

A nucleic acid construct of the invention may suitably be of genomic or cDNA origin, for instance obtained by preparing a genomic or cDNA library and screening for DNA sequences coding for all or part of the peptide by hybridization using synthetic oligonucleotide probes in accordance with standard techniques (cf. J. Sambrook et al, 1989, *Molecular Cloning, A Laboratory Manual,* 2d edition, Cold Spring Harbor, N.Y.) and by introducing the relevant mutations as it is known in the art.

A nucleic acid construct of the invention may also be prepared synthetically by established standard methods, e.g. the phosphoamidite method described by Beaucage and Caruthers, Tetrahedron Letters 22, 1859-1869 (1981), or the method described by Matthes et al., EMBO Journal 3, 801-805 (1984). According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or Saiki et al., Science 239, 487-491 (1988).

In one embodiment, the nucleic acid construct of the invention is a DNA construct which term will be used exclusively in the following for convenience. The statements in the following may also read on other nucleic acid constructs of the invention with appropriate adaptions as it will be clear for a person skilled in the art.

In one embodiment, the present invention relates to a recombinant vector comprising a DNA, or nucleic acid, construct of the invention. The recombinant vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector may be an expression vector in which the DNA sequence encoding the peptide of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the peptide.

The promoter may be any DNA sequence which shows transcriptional activity in the host cell of choice and may be derived from genes encoding proteins either homologous or heterologous to the host cell.

Examples of suitable promoters for use in yeast host cells include promoters from yeast glycolytic genes (Hitzeman et al., J. Biol. Chem. 255, 12073-12080 (1980); Alber and Kawasaki, J. Mol. Appl. Gen. 1, 419-434 (1982)) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304, 652-654 (1983)) promoters.

Examples of suitable promoters for use in filamentous fungus host cells are, for instance, the ADH3 promoter (McKnight et al., The EMBO J. 4, 2093-2099 (1985)) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizo-mucor miehei* lipase, *A. oryzae* alkaline protease, *A. oryzae* triose phosphate isomerase or *A. nidulans* acetamidase. In one embodiment, the promoter of a vector according to the invention is selected from the TAKA-amylase or the gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylosidase gene, or by the phage Lambda $P_R$ or $P_L$ promoters or the *E. coli* lac, trp or tac promoters.

The DNA sequence encoding the peptide of the invention may also, if necessary, be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 E1b region), transcriptional enhancer sequences (e.g. the SV40 enhancer) and translational enhancer sequences (e.g. the ones encoding adenovirus VA RNAs).

The recombinant vector of the invention may further comprise a DNA sequence enabling the vector to replicate in the host cell in question.

When the host cell is a yeast cell, suitable sequences enabling the vector to replicate are the yeast plasmid 2p replication genes REP 1-3 and origin of replication.

When the host cell is a bacterial cell, sequences enabling the vector to replicate are DNA polymerase III complex encoding genes and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 125-130 (1985)), or one which confers resistance to a drug, e.g. ampicillin, kanamycin, tetracyclin, chloramphenicol, neomycin, hygromycin or methotrexate. For filamentous fungi, selectable markers include amdS, pyrG, arqB, niaD and sC.

To direct a peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

For secretion from yeast cells, the secretory signal sequence may encode any signal peptide which ensures efficient direction of the expressed peptide into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., Nature 289 643-646 (1981)), a modified carboxypeptidase signal peptide (cf. L. A. Valls et al., Cell 48, 887-897 (1987)), the yeast BAR1 signal peptide (cf. WO 87/02670), or the yeast aspartic protease 3 (YAP3) signal peptide (cf. M. Egel-Mitani et al., Yeast 6, 127-137 (1990)).

For efficient secretion in yeast, a sequence encoding a leader peptide may also be inserted downstream of the signal sequence and upstream of the DNA sequence encoding the peptide. The function of the leader peptide is to allow the expressed peptide to be directed from the endoplasmic reticulum to the Golgi apparatus and further to a secretory vesicle for secretion into the culture medium (i.e. exportation of the peptide across the cell wall or at least through the cellular membrane into the periplasmic space of the yeast cell). The leader peptide may be the yeast α-factor leader (the use of which is described in e.g. U.S. Pat. No. 4,546,082, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp.

amylase or glucoamylase, a gene encoding a *Rhizomucor miehei* lipase or protease or a *Humicola lanuginosa* lipase. The signal peptide may be derived from a gene encoding *A. oryzae* TAKA amylase, *A. niger* neutral α-amylase, *A. niger* acid-stable amylase, or *A. niger* glucoamylase.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., op.cit.).

The host cell into which the DNA construct or the recombinant vector of the invention is introduced may be any cell which is capable of producing the present peptide and includes bacteria, yeast, fungi and higher eukaryotic cells. The present invention also related to a host cell comprising a nucleic acid construct according to the present invention, or a vector according to the present invention.

Examples of bacterial host cells which, on cultivation, are capable of producing the peptide of the invention are gram-positive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of *Streptomyces*, such as *S. lividans* or *S. murinus*, or gramnegative bacteria such as *Echerichia coli*. The transformation of the bacteria may be effected by protoplast transformation or by using competent cells in a manner known per se (cf. Sambrook et al., supra). Other suitable hosts include *S. mobaraense, S. lividans*, and *C. glutamicum* (Appl. Microbiol. Biotechnol. 64, 447-454 (2004)).

When expressing the peptide in bacteria such as *E. coli*, the peptide may be retained in the cytoplasm, typically as insoluble granules (known as inclusion bodies), or may be directed to the periplasmic space by a bacterial secretion sequence. In the former case, the cells are lysed and the granules are recovered and denatured after which the peptide is refolded by diluting the denaturing agent. In the latter case, the peptide may be recovered from the periplasmic space by disrupting the cells, e.g. by sonication or osmotic shock, to release the contents of the periplasmic space and recovering the peptide.

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous proteins therefrom are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. An example of a vector for use in yeast is the POT1 vector disclosed in U.S. Pat. No. 4,931,373. The DNA sequence encoding the peptide of the invention may be preceded by a signal sequence and optionally a leader sequence, e.g. as described above. Further examples of suitable yeast cells are strains of *Kluyveromyces*, such as *K. lactis, Hansenula*, e.g. *H. polymorpha*, or *Pichia*, e.g. *P. pastoris* (cf. Gleeson et al., J. Gen. Microbiol. 132, 3459-3465 (1986); U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of proteins is described in, e.g., EP 272 277 and EP 230 023. The transformation of *F. oxysporum* may, for instance, be carried out as described by Malardier et al. Gene 78, 147-156 (1989).

When a filamentous fungus is used as the host cell, it may be transformed with the DNA construct of the invention, conveniently by integrating the DNA construct in the host chromosome to obtain a recombinant host cell. This will make it more likely that the DNA sequence will be stably maintained in the cell. Integration of the DNA constructs into the host chromosome may be performed according to conventional methods, e.g. by homologous or heterologous recombination.

The transformed or transfected host cell described above is then cultured in a suitable nutrient medium under conditions permitting the expression of the present peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of peptide in question.

Peptides of the present invention may be used to raise antibodies that specifically bind to the peptides of the present invention. In the present context, "antibodies" include monoclonal and polyclonal antibodies, and antigen-binding fragments thereof, such as $F(ab')_2$ and Fab fragments, including genetically engineered antibodies and humanized antibodies. Antibodies are said to be specific if they bind to a peptide of the present invention with a $K_a$ greater than or equal to $10^7$ $M^{-1}$. Methods for preparing antibodies are disclosed in e.g. Hurrell J. G. R. (Ed.) *Monoclonal Hybridoma Antibodies: Techniques and Applications*, CRC Press, Boca Raton, Fla., 1982 and Sambrok, *Molecular Cloning: A Laboratory Manual*, Cold Spring Harbour, N.Y., 1989.

In one embodiment, the invention relates to a specific antibody against a peptide of the present invention. In one embodiment, said antibody does not bind to hIL-21 or Met-hIL-21 or to any of the polypeptides described in International Application WO2004/112703 or any of the other prior art IL-21 peptides as described herein.

The following list is a non-limiting list of embodiments.

Embodiment 1: An isolated IL-21 peptide having a mutation in one or more amino acid residues as compared to an IL-21 peptide having the amino acid sequence of SEQ ID No.2, wherein the activation mediated by said peptide through the IL-21 receptor is altered as compared to an IL-21 peptide having the amino acid sequence of SEQ ID No. 2.

Embodiment 2: An isolated IL-21 peptide having a mutation in one or more of the amino acid residues involved in the binding of IL-21 to the common gamma chain ($\gamma_c$) of the IL-21 receptor, wherein the activation mediated by said peptide through the IL-21 receptor is altered as compared to an IL-21 peptide having the amino acid sequence of SEQ ID No. 2.

Embodiment 3: An isolated IL-21 peptide having a mutation in one or more of the amino acid residues involved in the binding of IL-21 to the common gamma chain ($\gamma_c$) of the IL-21 receptor, wherein the IL-21 peptide has an altered binding to the IL-21 receptor as compared to an IL-21 peptide having the amino acid sequence of SEQ ID No. 2.

Embodiment 4: An isolated IL-21 peptide having a mutation in one or more of the amino acid residues involved in the binding of IL-21 to the common gamma chain ($\gamma_c$) of the IL-21 receptor, wherein said IL-21 peptide has an altered binding to the $\gamma_c$ of the IL-21 receptor as compared to an IL-21 peptide having the amino acid sequence of SEQ ID No. 2.

Embodiment 5: An isolated IL-21 peptide according to embodiment 1 or embodiment 2, wherein the activation mediated by said peptide through the IL-21 receptor is decreased as compared to an IL-21 peptide having the amino acid sequence of SEQ ID No. 2.

Embodiment 6: An isolated peptide according to embodiment 3, wherein the binding of said peptide to the IL-21 receptor is decreased as compared to an IL-21 peptide having the amino acid sequence of SEQ ID No. 2.

Embodiment 7: An isolated peptide according to embodiment 4, wherein the binding of said peptide to the $\gamma_c$ of the IL-21 receptor is decreased as compared to an IL-21 peptide having the amino acid sequence of SEQ ID No. 2.

Embodiment 8: An isolated peptide according to any of embodiments 5 to 7, wherein said peptide is an antagonist of the IL-21 receptor.

Embodiment 9: An isolated peptide according to embodiment 8, wherein the introduction of said mutation(s) is responsible for or contributory to the antagonistic activity of the IL-21 peptide.

Embodiment 10: An isolated peptide according to embodiment 8 or embodiment 9, wherein said peptide carries one or more antagonistic mutations in the region corresponding to Helix D of SEQ ID No. 1.

Embodiment 11: An isolated peptide according to embodiment 10, wherein one or more of said antagonistic mutations in Helix D is a mutation in one or more of the amino acid residues corresponding to positions Gln-116 and Ile-119 in SEQ ID No. 2.

Embodiment 12: An isolated peptide according to embodiment 11, wherein Gln-116 has been substituted with an Asp.

Embodiment 13: An isolated peptide according to embodiment 11 or embodiment 12, wherein Ile-119 has been substituted with an Asp.

Embodiment 14: An isolated peptide according to any of embodiments 8 to 12, wherein the amino acid residues corresponding to positions Ile-119 to Ser-133 has been deleted.

Embodiment 15: An isolated peptide according to any of embodiments 5 to 7, wherein said peptide is an agonist of the IL-21 receptor.

Embodiment 16: An isolated peptide according to 15, wherein said peptide carries one or more of the IL-21 mutations as described in WO2004112703.

Embodiment 17: An isolated peptide according to embodiment 15 or embodiment 16, wherein one or more of the amino acids in the region corresponding to amino acid residue 65 to 96 in SEQ ID No. 2 has been deleted or substituted.

Embodiment 18: An isolated peptide according to embodiment 17, wherein one or more of the amino acids in the region corresponding to amino acid residue 83 to 86 in SEQ ID No. 2 has been deleted or substituted.

Embodiment 19: An isolated peptide according to embodiment 17, wherein one or more of the amino acids in the region corresponding to amino acid residue 83 to 88 in SEQ ID No. 2 has been deleted or substituted.

Embodiment 20: An isolated peptide according to embodiment 17, wherein one or more of the amino acids in the region corresponding to amino acid residue 83 to 90 in SEQ ID No. 2 has been deleted or substituted.

Embodiment 21: An isolated peptide according to embodiment 17, wherein one or more of the amino acids in the region corresponding to amino acid residue 82 to 88 in SEQ ID No. 2 has been deleted or substituted.

Embodiment 22: An isolated peptide according to embodiment 17, wherein one or more of the amino acids in the region corresponding to amino acid residue 77 to 92 in SEQ ID No. 2 has been deleted or substituted.

Embodiment 23: An isolated peptide according to embodiment 17, wherein one or more of the amino acids in the region corresponding to amino acid residue 71 to 92 in SEQ ID No. 2 has been deleted or substituted.

Embodiment 24: An isolated peptide according to embodiment 17, wherein one or more of the amino acids in the region corresponding to amino acid residue 65 to 92 in SEQ ID No. 2 has been deleted or substituted.

Embodiment 25: An isolated peptide according to embodiment 17, wherein one or more of the amino acids in the region corresponding to amino acid residue 77 to 96 in SEQ ID No. 2 has been deleted or substituted.

Embodiment 26: An isolated peptide according to embodiment 17, wherein one or more of the amino acids in the region corresponding to amino acid residue 83 to 86 in SEQ ID No. 2 has been deleted or substituted.

Embodiment 27: An isolated peptide according to embodiment 17, wherein one or more of the amino acids in the region corresponding to amino acid residue 83 to 88 in SEQ ID No. 2 has been deleted or substituted.

Embodiment 28: An isolated peptide according to embodiment 17, wherein one or more of the amino acids in the region corresponding to amino acid residue 83 to 90 in SEQ ID No. 2 has been deleted or substituted.

Embodiment 29: An isolated peptide according to embodiment 17, wherein one or more of the amino acids in the region corresponding to amino acid residue 82 to 88 in SEQ ID No. 2 has been deleted or substituted.

Embodiment 30: An isolated peptide according to embodiment 17, wherein one or more of the amino acids in the region corresponding to amino acid residue 77 to 92 in SEQ ID No. 2 has been deleted or substituted.

Embodiment 31: An isolated peptide according to embodiment 17, wherein one or more of the amino acids in the region corresponding to amino acid residue 71 to 92 in SEQ ID No. 2 has been deleted or substituted.

Embodiment 32: An isolated peptide according to embodiment 17, wherein one or more of the amino acids in the region corresponding to amino acid residue 65 to 92 in SEQ ID No. 2 has been deleted or substituted.

Embodiment 33: An isolated peptide according to embodiment 17, wherein one or more of the amino acids in the region corresponding to amino acid residue 77 to 96 in SEQ ID No. 2 has been deleted or substituted.

Embodiment 34: An isolated IL-21 peptide according to embodiment 1 or embodiment 2, wherein the activation mediated by said peptide through the IL-21 receptor is increased as compared to an IL-21 peptide having the amino acid sequence of SEQ ID No. 2.

Embodiment 35: An isolated peptide according to embodiment 3, wherein the binding of said peptide to the IL-21 receptor is increased as compared to an IL-21 peptide having the amino acid sequence of SEQ ID No. 2.

Embodiment 36: An isolated peptide according to embodiment 4, wherein the binding of said peptide to the $\gamma_c$ of the IL-21 receptor is decreased as compared to an IL-21 peptide having the amino acid sequence of SEQ ID No. 2.

Embodiment 37: An isolated peptide according to any of embodiments 34 to 36, wherein said peptide is an antagonist of the IL-21 receptor.

Embodiment 38: An isolated peptide according to embodiment 37, wherein said peptide carries one or more antagonistic mutations in the region corresponding to Helix D of SEQ ID No. 2.

Embodiment 39: An isolated peptide according to embodiment 38, wherein one or more of said antagonistic mutations in Helix D is a mutation in one or more of the amino acid residues corresponding to positions Gln-116 and Ile-119 in SEQ ID No. 2.

Embodiment 40: An isolated peptide according to embodiment 39, wherein Gln-116 has been substituted with an Asp.

Embodiment 41: An isolated peptide according to embodiment 39 or embodiment 40, wherein Ile-119 has been substituted with an Asp.

Embodiment 42: An isolated peptide according to any of embodiments 37 to 40, wherein the amino acid residues corresponding to positions Ile-119 to Ser-133 has been deleted.

Embodiment 43: An isolated peptide according to any of embodiments 34 to 36, wherein said peptide is an agonist of the IL-21 receptor.

Embodiment 44: An isolated peptide according to embodiment 43, wherein said peptide carries one or more of the mutations as described in WO2004112703.

Embodiment 45: An isolated peptide according to embodiment 43 or embodiment 44, wherein one or more of the amino acids in the region corresponding to amino acid residue 65 to 96 in SEQ ID No. 2 has been deleted or substituted.

Embodiment 46: An isolated peptide according to embodiment 45, wherein one or more of the amino acids in the region corresponding to amino acid residue 83 to 86 in SEQ ID No. 2 has been deleted or substituted.

Embodiment 47: An isolated peptide according to embodiment 45, wherein one or more of the amino acids in the region corresponding to amino acid residue 83 to 88 in SEQ ID No. 2 has been deleted or substituted.

Embodiment 48: An isolated peptide according to embodiment 45, wherein one or more of the amino acids in the region corresponding to amino acid residue 83 to 90 in SEQ ID No. 2 has been deleted or substituted.

Embodiment 49: An isolated peptide according to embodiment 45, wherein one or more of the amino acids in the region corresponding to amino acid residue 82 to 88 in SEQ ID No. 2 has been deleted or substituted.

Embodiment 50: An isolated peptide according to embodiment 45, wherein one or more of the amino acids in the region corresponding to amino acid residue 77 to 92 in SEQ ID No. 2 has been deleted or substituted.

Embodiment 51: An isolated peptide according to embodiment 45, wherein one or more of the amino acids in the region corresponding to amino acid residue 71 to 92 in SEQ ID No. 2 has been deleted or substituted.

Embodiment 52: An isolated peptide according to embodiment 45, wherein one or more of the amino acids in the region corresponding to amino acid residue 65 to 92 in SEQ ID No. 2 has been deleted or substituted.

Embodiment 53: An isolated peptide according to embodiment 45, wherein one or more of the amino acids in the region corresponding to amino acid residue 77 to 96 in SEQ ID No. 2 has been deleted or substituted.

Embodiment 54: An isolated peptide according to embodiment 45, wherein one or more of the amino acids in the region corresponding to amino acid residue 83 to 86 in SEQ ID No. 2 has been deleted or substituted.

Embodiment 55: An isolated peptide according to embodiment 45, wherein one or more of the amino acids in the region corresponding to amino acid residue 83 to 88 in SEQ ID No. 2 has been deleted or substituted.

Embodiment 56: An isolated peptide according to embodiment 45, wherein one or more of the amino acids in the region corresponding to amino acid residue 83 to 90 in SEQ ID No. 2 has been deleted or substituted.

Embodiment 57: An isolated peptide according to embodiment 45, wherein one or more of the amino acids in the region corresponding to amino acid residue 82 to 88 in SEQ ID No. 2 has been deleted or substituted.

Embodiment 58: An isolated peptide according to embodiment 45, wherein one or more of the amino acids in the region corresponding to amino acid residue 77 to 92 in SEQ ID No. 2 has been deleted or substituted.

Embodiment 59: An isolated peptide according to embodiment 45, wherein one or more of the amino acids in the region corresponding to amino acid residue 71 to 92 in SEQ ID No. 2 has been deleted or substituted.

Embodiment 60: An isolated peptide according to embodiment 45, wherein one or more of the amino acids in the region corresponding to amino acid residue 65 to 92 in SEQ ID No. 2 has been deleted or substituted.

Embodiment 61: An isolated peptide according to embodiment 45, wherein one or more of the amino acids in the region corresponding to amino acid residue 77 to 96 in SEQ ID No. 2 has been deleted or substituted.

Embodiment 62: An isolated IL-21 peptide according to any of embodiments 1 to 44 having a mutation in one or more of the amino acid residues corresponding to Met-7, Arg-11, Ile-14, Asp-18, Glu-36, Asp-37, Thr-40, Glu-100, Glu-109 Ser-113, Gln-116, Lys-117, Ile-119, His-120, Lys-123, Ser-125, Arg-126, Thr-127, His-128, Gly-129, Ser-130, Glu-131, Asp-132, and Ser-133 in SEQ ID No. 2.

Embodiment 63: An isolated IL-21 peptide according to embodiment 62 having a mutation in one or more of the amino acid residues corresponding to Met-7, Arg-11, Ile-14, Asp-18, Glu-100, Glu-109, Ser-113, Gln-116, Lys-117, Ile-119, His-120, and Leu-123 in SEQ ID No. 2.

Embodiment 64: An isolated IL-21 peptide according to embodiment 62 having a mutation in one or more of the amino acid residues corresponding to Met-7, Arg-11, Ile-14, Asp-18, Glu-36, Asp-37, Thr-40, Glu-100, Ser-125, Arg-126, Thr-127, His-128, Gly-129, Ser-130, Glu-131, Asp-132, and Ser-133 in SEQ ID No. 2.

Embodiment 65: An isolated IL-21 peptide according to embodiment 62 having a mutation in one or more of the amino acid residues corresponding to Arg-11, Glu-36, Asp-37, Thr-40, Glu-100, Ser-113, Lys-117, and His-120 in SEQ ID No. 2.

Embodiment 66: An isolated IL-21 peptide according to embodiment 65 having a mutation in one or more of the amino acid residues corresponding to Ile-14, Gln-116, and Lys-117 in SEQ ID No. 2.

Embodiment 67: An isolated IL-21 peptide according to any of embodiments 1 to 66, wherein said peptide comprises a mutation in one or more of the amino acid residues in the region corresponding to Helix A in SEQ ID No. 1.

Embodiment 68: An isolated IL-21 peptide according to embodiment 67, wherein said peptide comprises a mutation in one or more of the amino acid residues corresponding to positions Met-7, Arg-11, Ile-14 and Asp-18.

Embodiment 69: An isolated IL-21 peptide according to any of embodiments 1 to 68, wherein said peptide comprises a mutation in one or more of the amino acid residues in the region corresponding to loop NB in SEQ ID No. 1.

Embodiment 70: An isolated IL-21 peptide according to embodiment 69, wherein said peptide comprises a mutation in one or more of the amino acid residues corresponding to positions Glu-36, Asp-37 and Thr-40 in SEQ ID No. 2.

Embodiment 71: An isolated IL-21 peptide according to any of embodiments 1 to 70, wherein said peptide comprises a mutation in one or more of the amino acid residues in the region corresponding to loop C/D in SEQ ID No. 1.

Embodiment 72: An isolated IL-21 peptide according to embodiment 71, wherein said peptide comprises a mutation in position Glu-100 in SEQ ID No. 2.

Embodiment 73: An isolated IL-21 peptide according to any of embodiments 1 to 72, wherein said peptide comprises a mutation in one or more of the amino acid residues in the region corresponding to Helix D in SEQ ID No. 1.

Embodiment 74: An isolated IL-21 peptide according to embodiment 73, wherein said peptide comprises a mutation in one or more of the amino acid residues corresponding to positions Glu-109 Ser-113, Gln-116, Lys-117, Ile-119, His-120, and Lys-123 in SEQ ID No. 2.

Embodiment 75: An isolated IL-21 peptide according to any of embodiments 1 to 72, wherein said peptide comprises a mutation in one or more of the amino acid residues in the ten most C-terminal amino acid residues.

Embodiment 76: An isolated IL-21 peptide according to embodiment 75, wherein said peptide comprises a mutation in one or more of the amino acid residues corresponding to positions Ser-125, Arg-126, Thr-127, His-128, Gly-129, Ser-130, Glu-131, Asp-132, and Ser-133 in SEQ ID No. 2.

Embodiment 77: An isolated IL-21 peptide according to any of embodiments 1 to 76, wherein the mutation in the stated position is a substitution with Ala.

Embodiment 78: An isolated IL-21 peptide according to any of embodiments 1 to 77 for use in therapy.

Embodiment 79: A pharmaceutical composition comprising a peptide according to any of embodiments 1 to 78.

Embodiment 80: Use of a peptide according to any of embodiments 1 to 78 or a pharmaceutical composition according to embodiment 79 for use in therapy.

Embodiment 81: Use of a peptide according to any of embodiments 1 to 78 or a pharmaceutical composition according to embodiment 79, wherein the IL-21 peptide is an antagonist of the IL-21 receptor, for use in treating a disease or disorder, wherein said disease or disorder may be treatable by use of an IL-21 antagonist.

Embodiment 82: Use of a peptide according to any of embodiments 1 to 78, wherein the IL-21 peptide is an antagonist of the IL-21 receptor, for preparation of a pharmaceutical composition for treating a disease or disorder, wherein said disease or disorder may be treatable by use of an IL-21 antagonist.

Embodiment 83: Use according to embodiment 81 or embodiment 82, wherein said disease or disorder is an autoimmune and/or inflammatory disease.

Embodiment 84: Use according to embodiment 83, wherein said disease or disorder is systemic lupus erythematosus, rheumatoid arthritis, inflammatory bowel disease or multiple sclerosis.

Embodiment 85: A method for the treatment of a disease or disorder, wherein said disease or disorder may be treatable by use of an IL-21 antagonist, wherein said treatment comprises the administration of an effective amount of a peptide according to any of embodiments 1 to 78, wherein said IL-21 peptide is an antagonist of the IL-21 receptor, to a patient in need thereof.

Embodiment 86: A method according to embodiment 85, wherein said disease or disorder is an autoimmune and/or inflammatory disease.

Embodiment 87: A method according to embodiment 86, wherein said disease or disorder is systemic lupus erythematosus, rheumatoid arthritis or inflammatory bowel disease.

Embodiment 88: Use of a peptide according to any of embodiments 1 to 78 or a pharmaceutical composition according to embodiment 79, wherein the IL-21 peptide is an agonist of the IL-21 receptor, for use in treating a disease or disorder, wherein said disease or disorder may be treatable by use of an IL-21 agonist.

Embodiment 89: Use of a peptide according to any of embodiments 1 to 78, wherein the IL-21 peptide is an agonist of the IL-21 receptor, for preparation of a pharmaceutical composition for treating a disease or disorder, wherein said disease or disorder may be treatable by use of an IL-21 agonist.

Embodiment 90: Use according to embodiment 88 or 89, wherein said disease or disorder is cancer.

Embodiment 91: Use according to embodiment 90, wherein said cancer is selected from non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin.

Embodiment 92: A use according to embodiment 91, wherein said cancer is malignant melanoma.

Embodiment 93: A method for the treatment of a disease or disorder, wherein said disease or disorder may be treatable by use of an IL-21 agonist, wherein said treatment comprises the administration of an effective amount of a peptide according to any of embodiments 1 to 78, wherein said IL-21 peptide is an agonist of the IL-21 receptor, to a patient in need thereof.

Embodiment 94: A method according to embodiment 93, wherein said disease or disorder is cancer.

Embodiment 95: A method according to embodiment 94, wherein said cancer is selected from non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin.

Embodiment 96: A method according to embodiment 95, wherein said cancer is malignant melanoma.

Embodiment 97: An isolated nucleic acid construct encoding a peptide according to any of embodiments 1 to 78.

Embodiment 98: A vector comprising a nucleic acid construct according to embodiment 97.

Embodiment 99: A host cell comprising a nucleic acid construct according to embodiment 97, or a vector according to embodiment 98.

Embodiment 100: An antibody that specifically binds a peptide according to any of embodiments 1 to 78.

Embodiment 101: An antibody according to embodiment 100, which antibody does not bind to hIL-21 or Met-hIL-21.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Example 1

NMR Structure of Met-hIL-21
Protein Expression and Purification

Met-hIL-21 (SEQ ID No. 3) consists of the sequence of the mature human IL-21 determined by expression in mammalian cell culture with an extra methionine residue added N-terminally. The protein is numbered starting with $Gln^{30}$ in SEQ ID No. 1, corresponding to residue 1 in SEQ ID No. 2, as residue 1 according to the N-terminus determined for the protein when expressed recombinantly in mammalian cells. The additional methionine residue present at the N-terminal when proteins are expressed intracellulary in E. coli thus becomes residue $Met^0$.

Met-hIL-21 was expressed as insoluble inclusion bodies in E. coli using the vector pET11c (the sequence inserted into this expression vector corresponds to the cDNA of the mature IL-21 protein with an extra methionine added N-terminally—the restriction sites NdeI and BamHI were used for this purpose).in a minimal medium with $^{15}NH_4SO_4$ or/and $[^{13}C_6]$-glucose as the main sources for nitrogen and carbon. Inclusion bodies were solubilized in 6 M guanidinium HCl, 100 mM TRIS, 40 mM DTT at pH 8.0 and refolded by dilution into a refolding buffer containing 0.75 M L-arginine, 40 mM Tris, 0.005% PEG 3350, 1.5 mM DTT, 4 mM Cystine, 20 mM NaCl, 4 mM $MgCl_2$, 1 mM KCl, 4 mM $CaCl_2$ at pH 7.5 and left overnight at 15° C. with slow stirring. Refolding was stopped by adjusting pH to 5.5 with acetic acid following by four-fold dilution into 25 mM sodium acetate pH 5.5. Misfolded Met-hIL-21 was allowed to precipitate and removed by filtration.

Refolded Met-hIL-21 was captured on a TosoHaas SP550C column and eluted with 1 M NaCl at pH 5.5 using a step gradient. Fractions with Met-hIL-21 were pooled and diluted ten-fold with 10 mM Tris pH 8.5 before loaded onto a Sepharose SP column. Met-hIL-21 was eluted using a linear gradient from 0.1 M to 1M NaCl in 25 mM Tris at pH 5.5. Fractions with Met-hIL-21 were pooled and concentrated with a Centriprep centrifugal filter from Millipore (cutoff 10 kDa). The concentrated Met-hIL-21 was loaded onto Superdex75 gelfiltration column equilibrated in 20 mM phosphate, 50 mM NaCl at pH 5.5. All chromatographic steps were run at 4° C.

Uniformly $^{15}N$ and $^{15}N/^{13}C$ labelled NMR samples (0.2-2.0 mM) were prepared in 50 mM NaCl, 20 mM phosphate, 1 mM $NaN_3$ at pH 5.5 (90% $H_2O$/10% $D_2O$) using Amicon Ultra-4 (cutoff 10 kDa). Sample homogeneity was analyzed by SDS PAGE and was for all samples >95%.

NMR Experiments

Unless otherwise specified, NMR spectra were acquired at 27° C. on a Bruker Avance 600 MHz spectrometer equipped with a 5 mm $^1H$ $\{^{15}N, ^{13}C\}$ TXI probe. 1D $^1H$ spectra were acquired for Met-hIL-21 samples with concentrations in the range 0.2-2.0 mM.

Sequential backbone assignments were done using established methods as described in Yamazaki, T. et al., Journal of the American Chemical Society 116, 11655-11666 (1994) and Hyberts, S. G. et al., Journal of Biomolecular NMR 26, 335-344 (2003). Assignment of side chain resonances included use of HN(CO)HAHB, H(C)(CCCO)NH, (H)C (CCCO)NH, H(C)CH-TOCSY and (H)CCH-TOCSY spectra as well as $^{15}N$- and $^{13}C$-edited NOESY-HSQC spectra. The $^{15}N$- and $^{13}C$-edited NOESY-HSQC spectra were acquired on a Varian Inova 800 MHz spectrometer equipped with a 3 mm triple resonance probe and on a Bruker Avance 600 MHz spectrometer equipped with a 5 mm $^1H$ $\{^{15}N, ^{13}C\}$ TXI cryoprobe, respectively.

Temperature studies were performed by acquiring $^{15}N$—HSQC spectra at temperatures between 10 and 50° C. Control spectra at 27° C. were acquired before and after the experiments. $^{15}N$—HSQC type exchange experiments were acquired with mixing times ranging from 0 to 1000 ms. Experiments measuring backbone amide $^{15}N$ $T_1$ and $T_2$ relaxation times and heteronuclear $\{^1H\}$—$^{15}N$ NOEs were acquired on a Bruker Avance 600 MHz spectrometer equipped with a 5 mm $^1H$ $\{^{15}N, ^{13}C\}$ TXI cryoprobe. $T_1$ and $T_2$ values were determined by least-square fitting of signal intensities to an exponential curve. Heteronuclear $\{^1H\}$—$^{15}N$ NOEs were calculated as the intensity ratios between $^{15}N$—HSQC spectra recorded with and without proton saturation.

Resolution of the Met-hIL-21 Structure by NMR

The $^{15}N$ HSQC spectra recorded for Met-hIL-21 display a fairly good dispersion despite a number of signals at random coil chemical shift values. These latter signals are due to the presence of flexible regions in the Met-hIL-21 molecule. Dilution experiments reveal no signs of aggregation in the range of 0.2-2.0 mM Met-hIL-21. Only minor changes were observed in $^{15}N$ HSQC spectra acquired at different pH values and salt concentrations (pH between 5.0-7.0 and NaCl between 0-100 mM).

Backbone resonances were assigned on the basis of a standard set of three-dimensional experiments (Yamazaki. T. et al., Journal of the American Chemical society 161, 11655-11666 (1994)), which were acquired using a uniformly $^{15}$N/$^{13}$C-labelled IL-21 sample. More than 96% of backbone resonances (N, HN, CA, HA, and CO) were assigned. Surprisingly, for residues Ser$^{57}$ to Gly$^{84}$ two distinct signals were observed for each residue demonstrating the presence of two different species of IL-21. Side chain reso-nance assignments are nearly complete (excluding the minor form at 27° C. of Ser$^{57}$ to Gly$^{84}$ with only 23 non-labile protons missing.

A plot of the difference between the observed chemical shifts and the tabulated values for random coil chemical shifts for backbone CA atoms (Wishart, D. S. et al. Journal of Biomolecular NMR 5, 67-81 (1995) against sequence number is shown in FIG. 1. Here four regions displaying positive secondary chemical shift reveal the presence and the position of the four α-helices (A, B, C and D) observed within the major the major form of Met-hIL-21. Helices A (Met$^7$-Asp$^{26}$) and D (Pro$^{104}$. Ser$^{124}$) are significantly longer than the helices B (Trp$^{44}$-Lys$^{52}$) and C (Asn$^{63}$-Lys$^{73}$). In the minor form of Met-hIL-21 at 27° C., the segment Ser$^{57}$ to Gly$^{84}$ shows no sign of helical structure (FIG. 1) suggesting that an extended, unordered conformation of this segment, which includes the helix C sequence, is adopted by this conformer.

A total of 1235, 2994 and 449 peaks from $^{15}$N-separated, $^{13}$C-separated NOESY and 2D NOESY spectra, respectively, were included in structure calculations. Peaks from the unfolded form of helix C (see below) were not included in these calculations. Together with chemical shifts for the assigned resonances, the NOEs were analyzed with Cyana using the candid protocol for automatic NOE assignment and structure calculation (Herrmann, T. Journal of Molecular Biology 319, 209-227 (2002)). Initial structure calculations were used to calibrate upper distance limits. Subsequently, all peak intensities were down-scaled by a factor of two to avoid effects on peak intensities due to the presence of the unfolded form.

Additional sources of structural information were included in the calculations. Thus two disulfide bonds were enforced between Cys$^{42}$ and Cys$^{93}$, and between Cys$^{49}$ and Cys$^{96}$. This disulfide pattern has been established for the Met-hIL-21 molecule through an analysis which combined protease cleavage, Edman degradation, and MS. Test calculations without disulfide bond constraints supported this pattern (not shown). Chemical shift values for HA, CA, CB, N and CO atoms were analyzed to predict phi and psi backbone angles using the computer program Talos (Cornilescu, G., et al., Journal of Biomolecular NMR 13, 289-302 (1999)). Talos gave good predictions for 78 residues, and 156 angle phi/psi angle constraints were included in the calculations with an uncertainty of ±30 degrees. From the HNHA spectrum 72 J(HA-HN) scalar coupling constants were extracted and included in the structure calculations. Hydrogen bond constraints were added for 20 backbone amide protons which exchange slowly in deuterium exchange experiments. Hydrogen bond pattern were identified based on structures calculated without hydrogen bond constraints.

Figure 2:
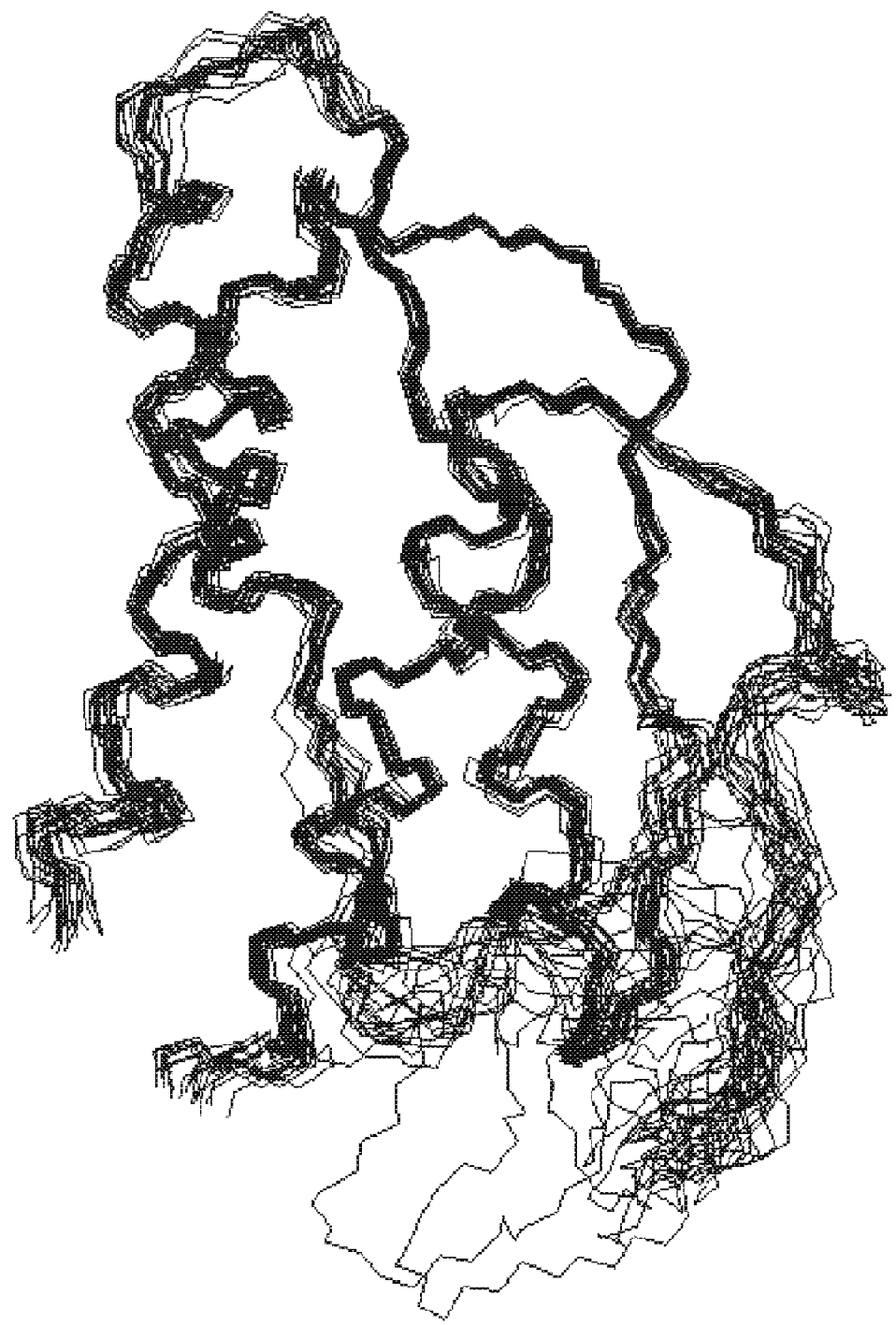
FIG. 2: Superposition of ensemble of the 20 structures with lowest energy from Cyana. Backbone atoms for residues $Met^{7}$-$Ser^{80}$ and $Cys^{93}$-$Ser^{124}$ were used for the superposition. Only backbone atoms are shown. N- and C-terminal residues $Met^{0}$-$His^{6}$ and $Ser^{125}$-$Ser^{133}$, respectively, have been removed for clarity.

An ensemble of 20 structures was calculated with Cyana (Table 1). No distance violations greater than 0.5 Å was observed. In only four cases was a dihedral constraint violated by more than 5 degrees. Segments of the protein at the N-terminus (Met$^0$-His$^6$) and at the C-terminus (Ser$^{124}$-Ser$^{133}$) are disordered as is part of the loop connecting helices C and D (Pro$^{79}$-Thr$^{92}$). Except for these regions the ensemble is well ordered with an RMSD of 0.64 Å for backbone heavy atoms (FIG. 2).

TABLE 1

Structural statistics for hIL-21

| Conformationally restricting distance constraints | |
|---|---|
| Intraresidue [i = j] | 209 |
| Sequential [(i − j) = 1] | 502 |
| Medium Range [2 ≤ (i − j) ≤ 5] | 496 |
| Long Range [6 ≤ (i − j)] | 548 |
| Total | 1755 |
| Dihedral angle constraints | 143 |
| Hydrogen-bond constraints | 40 |
| Disulfide bond constraints[a] | 12 |
| Constraints per residue | 14.6 |
| Long-range constraints per residue | 4.3 |
| Cyana target function [Å$^2$] | 1.01 ± 0.10 |
| Average RMSD to mean coordinates [Å] | |
| Residues 7-123, backbone heavy atoms | 1.22 |
| Residues 7-123, heavy atoms | 1.76 |
| Residues 7-78, 93-123, backbone heavy atoms | 0.64 |
| Residues 7-78, 93-123, heavy atoms | 1.11 |
| Secondary structure elements, backbone heavy atoms | 0.47 |
| Secondary structure elements, heavy atoms | 1.02 |
| Ramachandran plot summary for residues 7-78, 93-123 [%] | |
| Most favored regions | 74 |
| Additionally allowed regions | 23 |
| Generously allowed regions | 2 |
| Disallowed regions | 1 |
| Distance constraint violations per CYANA conformer | |
| 0.2-0.5 Å | 2.4 |
| >0.5 Å | 0 |
| Dihedral-angle constraint violations per CYANA conformer | |
| >5 degrees | 0.2 |

[a]Each disulfide bond is constrained by three upper and three lower bounds.

Example 2

Determining the Amino Acid Residues in IL-21 Involved in the Binding to $\gamma_c$ Resonances were assigned using a standard set of three-dimensional experiments (Yamazaki, T. et al., Journal of the American Chemical Society 116, 11655-11666 (1994)), which were acquired using a uniformly $^{15}$N/$^{13}$C-labelled Met-hIL-21 sample. A total of 1235, 2994 and 449 peaks from $^{15}$N-separated, $^{13}$C-separated NOESY and 2D NOESY spectra, respectively, were included in structure calculations. Together with chemical shifts for the assigned resonances, the NOEs were analyzed with Cyana using the candid protocol for automatic NOE assignment and structure calculation (Herrmann, T. et al., Journal of Molecular Biology 319, 209-227 (2002)). An ensemble of 20 structures was calculated with Cyana. Segments of the protein at the N-terminus (Met$^0$-His$^6$) and at the C-terminus (Ser$^{124}$-Ser$^{133}$) are disordered as is part of the loop connecting helices C and D (Pro$^{79}$-Thr$^{92}$). Except for these regions the ensemble is well ordered with an RMSD of 0.64 A for backbone heavy atoms.

The 3D model of the Met-hIL-21/h$\gamma_c$ receptor complex was constructed with the program Modeller (Sali, A. et al., Journal of Molecular Biology 234, 779-815 (1993).) using the crystal structure of the hIL-2/hIL-2Rα/hIL-2Rβ/h$\gamma_c$ complex (Wang, X. Q. et al., Science 310, 1159-1163 (2005)) and the NMR structure of IL-21 as templates. A structure based sequence alignment of hIL-2 and hIL-21 was performed with the program LSQMAN using the structure hIL-2 from the crystal structure of the hIL-2/hIL-2Rα/hIL-2Rβ/$\gamma_c$ complex, and the above mentioned NMR structure was used for IL-21. Subsequently, residues in IL-21 making hydrogen bond, salt bridges or vdw contacts with $\gamma_c$ in the model were identified, and these residues are M7, R11, I14, D18, E100, E108, S113, Q116, K117, I119, H120, and L123 in SEQ ID No. 2.

Example 3

Identification of Residues in hIL-21 Involved in Common Gamma Chain Binding

Two different approaches were used for identification of residues of hIL-12 involved in binding to common gamma chain.

First Approach

A structure based sequence alignment of the hIL-2/hIL-2Rα/hIL-2Rβ/$\gamma_c$ complex and hIL-21 was performed with the program LSQMAN using the crystal structure of the hIL-2/hIL-2Rα/hIL-2Rβ/$\gamma_c$ complex (Wang, X. Q. et al., Science 310, 1159-1163 (2005)), and using the NMR structure for IL-21 as elucidated in Example 1. Residues involved in the interaction between hIL-2 and $\gamma_c$ in the hIL-2/hIL-2Rα/hIL-2Rβ/$\gamma_c$ complex were taken from Table S2 c in supporting materials for Wang, X. Q. et al., Science 310, 1159-1163 (2005). Based on the sequence alignment (see FIG. 3), the corresponding residues in hIL-21 were identified. These residues are M7, R11, I14, D18, E100, E109, S113, Q116, K117, I119, H120, and L123 in SEQ ID No. 2.

Second Approach

A structure based sequence alignment of the hIL-2/hIL-2Rα/hIL-2Rβ/$\gamma_c$ complex, hIL-4/hIL-4Rα and hIL-21 was performed with the program LSQMAN. A sequence alignment of hIL2Rβ, hIL-4Rα and hIL-21Rα was created by hand and corrected manually during the modeling process. A model of the ternary hIL-21/hIL-21Rα/$\gamma_c$ complex was constructed with the program Modeller using the crystal structures of the hIL-2/hIL-2Rα/hIL-2Rβ/γ and hIL-4/hIL-4Rα complexes (Wang, X. Q. et al. Science 310, 1159-1163 (2005), Hage, T. et al., Cell 97, 271-281 (1999)) and the NMR structure of IL-21 as templates together with sequence alignment described above. Subsequently, residues in IL-21 making hydrogen bond, salt bridges or van der Weals contacts with $\gamma_c$ in the model were identified with the program MOE. These residues are R11, I14, E36, D37, T40, E106, E109, S113, Q116, K117, H120, S125, R126, T127, H128, G129, S130, E131, D132, and S133 in SEQ ID No. 2.

Excluding the C-terminal residues S125-S133 identified with the second approach, the two set of residue are close to identical. The C-terminal residues of hIL-21 cannot be identified with the first approach as hIL-2 has a truncated C-terminus compared to hIL-21. The final set of residues in hIL-21 involved in common gamma chain binding is defined as the combination of the two sets of residues. These residues are M7, R11, I14, D18, E36, D37, T40, E100, E106, E109, S113, Q116, K117, I119, H120, L123, S125, R126, T127, H128, G129, S130, E131, D132, and S133 in SEQ ID No. 2.

Example 4

Effects of Mutations on the Binding to the Receptor

Each of the aforementioned positions was investigated for their contribution to the overall binding of IL-21 to the receptor complex through individual mutational exchange. Thus an ala-scan mutagenesis was performed for each residue employing PCR-mediated mutagenesis. In the ala-scan analysis individual amino acid positions are, through mutagenesis, exchanged for an alanine residue. The mutants are expressed transiently in mammalian HEK293 cells and subsequently analyzed as supernatants using the assays as described below.

The Met-hIL-21 alanine substituted variants were subsequently expressed by transient transfection in HEK293 FS cells and supernatants from cells propagated in serum-free medium were analysed with respect to their ability to activate the IL-21 receptor complex. One such activity analysis is composed of whole cells in which IL-21 activity may be monitored through a Luciferase-based reporter system as described below.

Pharmacological Methods

Assay (Ia)

Activation of the IL-21 Receptor by IL-21 Peptides hIL-21 and IL-21 peptides according to the invention may be analyzed using in a cellular activity assay using a stat-regulated luciferase reporter system. The assay employs the murine Baf3 cell line, which has been stably transfected to express the human IL-21R and a Stat-linked luciferase reporter construct. The Baf3 cells expresses endogenously the $\gamma_c$ common chain. The Baf3/hIL-21R reporter cell line was starved in IL-3 free medium for 6 hours prior to stimulation. A dosis-response analysis was subsequently carried out using stimulation of the cells for 24 hours.

Assay (Ib)

Activation of the IL-21 Receptor by IL-21 Peptides

The cDNAs encoding the IL-21 peptides according to the invention may be analyzed by transient expression followed by activity analysis in a stat-regulated reporter system. The cDNAs were transfected into HEK293 FreeStyle cells (Stengaard-Pedersen et al. N. Engl. J. Med. 34, 554 (2003); Invitrogen). Supernatants were collected from serum-free medium at 48 hours post transfection and analyzed in a cellular bioassay. The assay employs the murine Baf3 cell line, stably transfected to express the human IL-21R and a Stat-linked luciferase reporter construct. The Baf3 cells expresses endogenously the γc component of the active IL-21 receptor complex. The Baf3/hIL-21R reporter cell line was starved in IL-3 free medium for 18 hours prior to stimulation. A dosis-response analysis was carried out using raw supernatant from the HEK293-FS tranfectants. Duration of the stimulation was four hours.

Assay (II)

Binding of IL-21 Peptide to the γ, of the IL-21 Receptor Complex.

The binding of IL-21 to the $\gamma_c$ chain is evaluated by surface plasmon resonance analysis employing BIAcore instrumentation (Pharmacia Biosensor). Here the $\gamma_c$ chain, in the form of for instance a $\gamma_c$-Fc fusion protein is first biotinylated and subsequently immobilized on a streptavidin-coated biosensor matrix. Buffer containing the hIL-21 peptide or variants thereof is passed over the matrix. From the resulting sensograms the kinetic constants reflecting on-rate and off-rate respectively is calculated as a result of at least three independent measurements performed using a concentration range of IL-21. From the kinetic konstants ($k_{on}$ and $K_{off}$), an apparent dissociation constant, $K_D$, may be calculated as a measure of binding affinity.

The invention claimed is:

1. An isolated IL-21 peptide comprising a mutation selected from the group consisting of the amino acid residues corresponding to Met-7, Arg-11, Ile-14, Asp-18, Glu-36, Asp-37, Thr-40, Glu-100, Glu-109, Ser-113, and Lys-117 in SEQ ID NO:2.

2. The peptide of claim 1 wherein the mutation consists of amino acid residue Met-7, Arg-11, Ile-14 or Asp-18 of SEQ ID. NO:2.

3. The peptide of claim 1 wherein the mutation consists of amino acid residue Glu-36, Asp-37 or Thr-40 of SEQ ID NO:2.

4. The peptide of claim 1 wherein the mutation consists of amino acid residue Glu-100 of SEQ ID. NO:2.

5. The peptide of claim 1, wherein the mutation consists of amino acid residue Glu-109, Ser-113 or Lys-117 of SEQ ID. NO:2.

6. The peptide of claim 1, further consisting of a deletion in one or more of amino acid residues 124 to 133 of SEQ ID. NO:2.

* * * * *

SEQUENCE LISTING

<160> NUMBER OF SEQ ID NOS: 3

<210> SEQ ID NO 1
<211> LENGTH: 162
<212> TYPE: PRT
<213> ORGANISM: Homo sapiens

<400> SEQUENCE: 1

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 2
<211> LENGTH: 133
<212> TYPE: PRT
<213> ORGANISM: Homo sapiens

<400> SEQUENCE: 2

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 3

```
<211> LENGTH: 134
<212> TYPE: PRT
<213> ORGANISM: Artificial Sequence
<220> FEATURE:
<223> OTHER INFORMATION: Human IL-21 with additional N-terminal
      methionine residue

<400> SEQUENCE: 3

Met Gln Gly Gln Asp Arg His Met Ile Arg Met Arg Gln Leu Ile Asp
1               5                   10                  15

Ile Val Asp Gln Leu Lys Asn Tyr Val Asn Asp Leu Val Pro Glu Phe
                20                  25                  30

Leu Pro Ala Pro Glu Asp Val Glu Thr Asn Cys Glu Trp Ser Ala Phe
            35                  40                  45

Ser Cys Phe Gln Lys Ala Gln Leu Lys Ser Ala Asn Thr Gly Asn Asn
    50                  55                  60

Glu Arg Ile Ile Asn Val Ser Ile Lys Lys Leu Lys Arg Lys Pro Pro
65                  70                  75                  80

Ser Thr Asn Ala Gly Arg Arg Gln Lys His Arg Leu Thr Cys Pro Ser
                85                  90                  95

Cys Asp Ser Tyr Glu Lys Lys Pro Pro Lys Glu Phe Leu Glu Arg Phe
                100                 105                 110

Lys Ser Leu Leu Gln Lys Met Ile His Gln His Leu Ser Ser Arg Thr
            115                 120                 125

His Gly Ser Glu Asp Ser
    130
```